(12) United States Patent
Liu et al.

(10) Patent No.: US 12,060,893 B2
(45) Date of Patent: Aug. 13, 2024

(54) PORTABLE BLOWING DEVICE

(71) Applicant: Shenzhen Lanhe Technologies Co., Ltd., Shenzhen (CN)

(72) Inventors: Kai Liu, Guangdong (CN); Xunhuan Wu, Guangdong (CN); Guang Yang, Guangdong (CN); Weiping Li, Shenzhen (CN); Jun Zhu, Shenzhen (CN); Quan Lv, Shenzhen (CN); You Lai, Shenzhen (CN); Tong Li, Shenzhen (CN)

(73) Assignee: SHENZHEN LANHE TECHNOLOGIES CO., LTD., Shenzhen (CN)

( * ) Notice: Subject to any disclaimer, the term of this patent is extended or adjusted under 35 U.S.C. 154(b) by 614 days.

(21) Appl. No.: 17/315,274

(22) Filed: May 8, 2021

(65) Prior Publication Data

US 2021/0355959 A1  Nov. 18, 2021
US 2022/0290687 A9  Sep. 15, 2022

Related U.S. Application Data

(63) Continuation-in-part of application No. PCT/CN2021/072345, filed on Jan. 16, 2021, and a
(Continued)

(30) Foreign Application Priority Data

Oct. 9, 2019 (CN) .......................... 201921684168.3
Jan. 18, 2020 (CN) .......................... 202020122560.5
(Continued)

(51) Int. Cl.
*F04D 29/42* (2006.01)
*A61F 7/00* (2006.01)
(Continued)

(52) U.S. Cl.
CPC ....... *F04D 29/424* (2013.01); *F04D 25/0673* (2013.01); *F04D 29/4246* (2013.01);
(Continued)

(58) Field of Classification Search
CPC ............... F04D 29/424; F04D 25/0673; F04D 29/4246; F04D 29/441; F25B 21/02; A61F 2007/0011
(Continued)

(56) References Cited

U.S. PATENT DOCUMENTS 5,802,865 A  9/1998 Strauss
6,189,327 B1  2/2001 Strauss et al.
(Continued)

FOREIGN PATENT DOCUMENTS

CN  202040104 U  11/2011
CN  103270315 A  8/2013
(Continued)

OTHER PUBLICATIONS

Foreign Ref (Year: 2024).*

*Primary Examiner* — Jon T. Schermerhorn, Jr.
(74) *Attorney, Agent, or Firm* — Andrew C. Cheng

(57) ABSTRACT

A portable blowing device includes a body and fans arranged in the body. Air channels are arranged in the body and extend in the length direction of the body to allow airflow to pass through. Wind shields are arranged in the air channels, and a periphery of the wind shield is closely connected with a side wall of the air channel so that a sub-air channel is formed between the wind shield and the side wall of the air channel. Air outlets are formed in the side wall for communicating with outside and the sub-air channel, and airflow generated by the fan can enter the sub-air channel and then exits the air outlets. Because of the reduced volume of the sub-air channel, the airflow is concentrated after
(Continued)

entering the sub-air channel, and airflow exiting the air outlets is strengthened, so that the cooling effect and the user experience are improved.

9 Claims, 27 Drawing Sheets

Related U.S. Application Data continuation-in-part of application No. PCT/CN2020/089050, filed on May 7, 2020, and a continuation-in-part of application No. PCT/CN2020/089049, filed on May 7, 2020, and a continuation-in-part of application No. PCT/CN2019/123073, filed on Dec. 4, 2019.

(30) Foreign Application Priority Data

| Jan. 19, 2020 | (CN) | 202020122804.X |
|---|---|---|
| Jan. 19, 2020 | (CN) | 202020135409.5 |
| May 13, 2020 | (CN) | 202020796618.4 |
| Aug. 25, 2020 | (CN) | 202021804208.6 |
| Dec. 31, 2020 | (CN) | 202011641197.9 |

(51) Int. Cl.
  F04D 25/06      (2006.01)
  F04D 29/44      (2006.01)
  F25B 21/02      (2006.01)

(52) U.S. Cl.
  CPC ............ *F04D 29/441* (2013.01); *F25B 21/02* (2013.01); *A61F 2007/0011* (2013.01)

(58) Field of Classification Search
  USPC ...................................................... 62/259.3
  See application file for complete search history.

(56) References Cited

U.S. PATENT DOCUMENTS

| 6,682,552 | B2 |  | 1/2004 | Ramsden et al. |  |
|---|---|---|---|---|---|
| 7,828,524 | B2 | * | 11/2010 | Chen .................. | F04D 25/084 |
|  |  |  |  |  | 415/206 |
| 10,570,920 | B2 | * | 2/2020 | Lee ...................... | F04D 25/08 |
| 10,709,601 | B2 | * | 7/2020 | Adair ...................... | A61F 7/02 |
| 11,187,241 | B1 | * | 11/2021 | Liu ...................... | F04D 29/441 |
| 11,319,960 | B2 | * | 5/2022 | Liu ...................... | F04D 29/282 |
| 11,624,370 | B2 | * | 4/2023 | Liu ...................... | F04D 29/582 |
|  |  |  |  |  | 415/203 |
| 11,635,083 | B2 | * | 4/2023 | Li ........................ | F04D 25/084 |
|  |  |  |  |  | 415/182.1 |
| 11,661,947 | B2 | * | 5/2023 | Li ............................ | A61F 7/02 |
|  |  |  |  |  | 415/182.1 |
| 11,754,080 | B2 | * | 9/2023 | Xie .......................... | A61F 7/02 |
|  |  |  |  |  | 415/182.1 |
| 11,795,957 | B2 | * | 10/2023 | Li ........................ | F04D 29/424 |
| 11,815,098 | B1 | * | 11/2023 | Patil ...................... | F25B 21/02 |
| 11,873,825 | B2 | * | 1/2024 | Liu ...................... | F04D 29/4226 |
| 2010/0198322 | A1 |  | 8/2010 | Joseph et al. |  |
| 2011/0259028 | A1 |  | 10/2011 | Lee |  |
| 2017/0035602 | A1 | * | 2/2017 | Shapiro .................. | A61F 7/007 |
| 2017/0266038 | A1 |  | 9/2017 | Peavy et al. |  |
| 2017/0370596 | A1 |  | 12/2017 | Lee |  |
| 2020/0187574 | A1 |  | 6/2020 | Te Hsiang |  |
| 2020/0309152 | A1 | * | 10/2020 | Sanford .................. | F04D 29/601 |
| 2022/0354206 | A1 | * | 11/2022 | Feher ...................... | A42B 3/285 |
| 2023/0098472 | A1 | * | 3/2023 | Cai ........................ | A62B 18/025 |
|  |  |  |  |  | 128/204.15 |
| 2024/0077082 | A1 | * | 3/2024 | Xie ........................ | F04D 29/424 |

FOREIGN PATENT DOCUMENTS

| CN | 104728130 | A |  | 6/2015 |  |
|---|---|---|---|---|---|
| CN | 205073111 | U |  | 3/2016 |  |
| CN | 206386293 | U |  | 8/2017 |  |
| CN | 208089598 | U |  | 11/2018 |  |
| CN | 109937305 | A |  | 6/2019 |  |
| CN | 209354401 | U |  | 9/2019 |  |
| CN | 209818363 | U |  | 12/2019 |  |
| CN | 110685939 | A |  | 1/2020 |  |
| CN | 210343802 | U |  | 4/2020 |  |
| CN | 210829801 | U |  | 6/2020 |  |
| CN | 211039122 | U |  | 7/2020 |  |
| CN | 211059041 | U | * | 7/2020 | ........... F04D 25/166 |
| CN | 211059041 | U |  | 7/2020 |  |
| CN | 211116729 | U |  | 7/2020 |  |
| CN | 211116730 | U |  | 7/2020 |  |
| CN | 211474489 | U |  | 9/2020 |  |
| CN | 211503086 | U |  | 9/2020 |  |
| CN | 110566482 | B |  | 10/2020 |  |
| CN | 111765125 | A |  | 10/2020 |  |
| CN | 211648516 | U |  | 10/2020 |  |
| CN | 211692897 | U |  | 10/2020 |  |
| CN | 211778092 | U |  | 10/2020 |  |
| CN | 211781697 | U | * | 10/2020 |  |
| CN | 212055205 | U |  | 12/2020 |  |
| CN | 212106302 | U |  | 12/2020 |  |
| CN | 212318329 | U |  | 1/2021 |  |
| CN | 212536127 | U |  | 2/2021 |  |
| CN | 212536132 | U |  | 2/2021 |  |
| CN | 212536134 | U |  | 2/2021 |  |
| CN | 212615490 | U |  | 2/2021 |  |
| CN | P12479643 | U |  | 2/2021 |  |
| CN | 212690401 | U |  | 3/2021 |  |
| CN | 212717253 | U |  | 3/2021 |  |
| CN | 212899063 | U |  | 4/2021 |  |
| CN | 213176099 | U |  | 5/2021 |  |
| CN | 218882596 | U | * | 4/2023 |  |
| JP | 3220810 | U |  | 4/2019 |  |
| JP | 2019105266 | A |  | 6/2019 |  |
| JP | 2023537542 | A | * | 11/2020 |  |
| JP | 6852140 | B1 |  | 3/2021 |  |
| JP | 2021076095 | A |  | 5/2021 |  |
| KR | 200484695 | Y1 |  | 10/2017 |  |
| KR | 101905697 | B1 |  | 10/2018 |  |
| KR | 200487688 | Y1 |  | 10/2018 |  |
| KR | 101936607 | B1 |  | 1/2019 |  |
| KR | 1020190041795 | A |  | 4/2019 |  |
| KR | 200489770 | Y1 |  | 7/2019 |  |
| KR | 200489770 | Y1 |  | 8/2019 |  |
| KR | 102047027 | B1 |  | 11/2019 |  |
| KR | 102243888 | B1 |  | 4/2021 |  |
| TW | 626408 | B |  | 6/2018 |  |
| WO | 2021068389 | A1 |  | 4/2021 |  |
| WO | WO-2021068389 | A1 | * | 4/2021 |  |
| WO | WO-2022032721 | A1 | * | 2/2022 |  |
| WO | WO-2022073279 | A1 | * | 4/2022 | ............ A61F 7/00 |

* cited by examiner

PORTABLE BLOWING DEVICE

CROSS REFERENCE TO RELATED APPLICATIONS

This application is a continuation-in-part of International (PCT) Patent Application 1) No. PCT/CN2020/089050, filed on May 7, 2020, which claims priority of China Patent Application No. 202020135409.5, filed on Jan. 19, 2020, 2) PCT/CN2020/089049, filed on May 7, 2020, which claims priority of China Patent Application No. 202020122804.X, filed on Jan. 19, 2020, 3) PCT/CN2021/072345, filed on Jan. 16, 2021, which claims priority of China Patent Application No. 202020122560.5, filed on Jan. 18, 2020 and 4) PCT/CN2019/123073 filed on Dec. 4, 2019, which claims priority of China Patent Application No. 201921684168.3, filed on Oct. 9, 2019. This application claims priority of China Patent Application No. 202021804208.6, filed on Aug. 25, 2020; China Patent Application No. 202020796618.4, filed on May 13, 2020; China Patent Application No. 202011641197.9, filed on Dec. 31, 2020. The contents of the above-identified applications are incorporated herein by reference.

TECHNICAL FIELD

The present disclosure relates to the technical field of cooling devices, in particular to a portable blowing device.

BACKGROUND

With people's growing request for a more convenient life in recent years, various portable fans such as neck fans have appeared in the market to meet the needs in outdoor activities or other life scenes. Neck fans break the activity limitation of hand-held fans. Whether it is during exercise and outdoor activities or in the office, neck fans can achieve the effect of blowing air anytime and anywhere while freeing users' hands.

An existing neck fan generally comprises a support for resting on the neck of a human body and a fan located in the support. An air channel corresponding to the fan is arranged in the support, air outlets communicating with the outside are arranged on a side wall of the air channel, and airflow generated by the fan enters the air channel and then is blown out from the air outlets, thereby cooling the neck of the human body. However, because the air channel of the existing fan is directly formed by an inner side wall of a housing of the support, the volume of the air channel is quite large, making the airflow generated by the fan dispersed after reaching the air channel, so the airflow blown out from the air outlets is weak and the cooling effect is poor, which affects the user experience.

BRIEF SUMMARY OF THE INVENTION

The purpose of this present disclosure is to provide an improved portable blowing device. By arranging a wind shield in an air channel of a support, a sub-air channel with a reduced volume is formed in the air channel. Airflow generated by the fan enters the sub-air channel and then is blown out from air outlets. Due to the volume of the sub-air channel is reduced compared to the air channel, the airflow generated by the fan is concentrated after entering the sub-air channel, and the airflow blown out from the air outlets is strengthened, so that the cooling effect and the user experience are improved.

In one aspect, the present disclosure provides a portable blowing device comprising a body for being hung around a neck of a human body and fans positioned in the body, wherein air channels corresponding to the fans are arranged in the body, and the air channels extend in the length direction of the body. A wind shield is arranged in the air channel, and the wind shield is closely connected with a part of a side wall of the air channel, so that a sub-air channel is formed between the wind shield and the other part of the side wall of the air channel. Air outlets communicating with the outside are formed in the side wall of the sub-air channel, and airflow generated by the fan enters the sub-air channel and then is blown out from the air outlets.

In another aspect, a portable blowing device comprises a body for being hung around a neck of a human body and fans located in the body. The body comprises a connector and a first support and a second support respectively connected to two ends of the connector. The fans and driving devices for driving the fans to run are respectively arranged in the first support and the second support. The first support and the second support each comprise an outer side wall away from the neck of the human body and an inner side wall close to the neck of the human body. The driving device in one of the first support and the second support is fixed on the outer side wall, and the driving device in the other of the first support and the second support is fixed on the inner side wall.

In yet another one aspect, the present disclosure further provides a portable blowing device comprising a body and fans arranged in the body. The body comprises supports. Air channels communicating with the fans are arranged in the supports. An air guiding member is arranged in the air channel to divide the air channel into a first air channel and a second air channel. A side wall of the support comprises a first section and a second section located on both sides of the air guiding member. The first section is provided with first air outlets communicating with the first air channel, and the second section is provided with second air outlets communicating with the second air channel.

Preferably, the support comprises an inner side wall close to the neck of the human body and an outer side wall away from the neck of the human body. The first air outlets and the second air outlets are arranged on the inner side wall. A starting end of the air guiding member divides an inlet of the air channel into a first air inlet and a second air inlet. The first air inlet and the second air inlet respectively communicate with the first air channel and the second air channel, and the area of the first air inlet is smaller than that of the second air inlet.

According to the portable blowing device provided in the present disclosure, the wind shield is arranged in the air channel of the support to make a portion of the air channel to form a sub-air channel which has a reduced cross-sectional area and therefore a reduced volume. Airflow generated by the fan enters the sub-air channel and then is blown out from the air outlets. Due to the reduced volume of the sub-air channel formed by the wind shield, the airflow generated by the fan is concentrated after entering the sub-air channel and wind blown out from the air outlets is strengthened, so that the cooling effect and the user experience are improved.

DETAILED DESCRIPTION OF THE INVENTION

Figure 1:
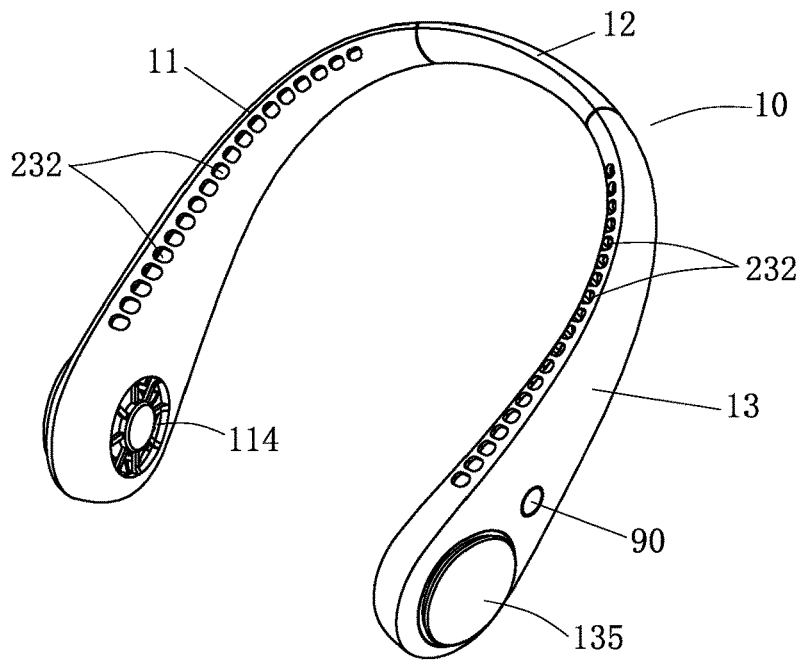
FIG. 1 is a perspective assembled view of a portable blowing device according to Embodiment 1 of the present disclosure.
Figure 2:
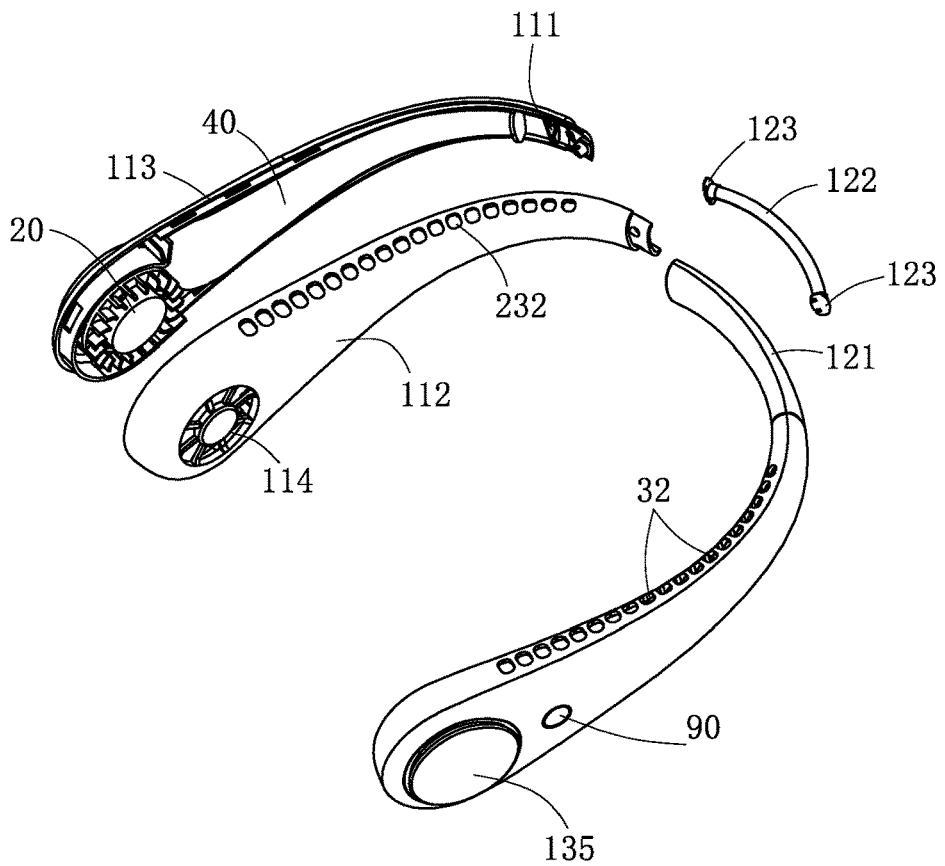
FIG. 2 is a partially exploded view of FIG. 1.
Figure 3:
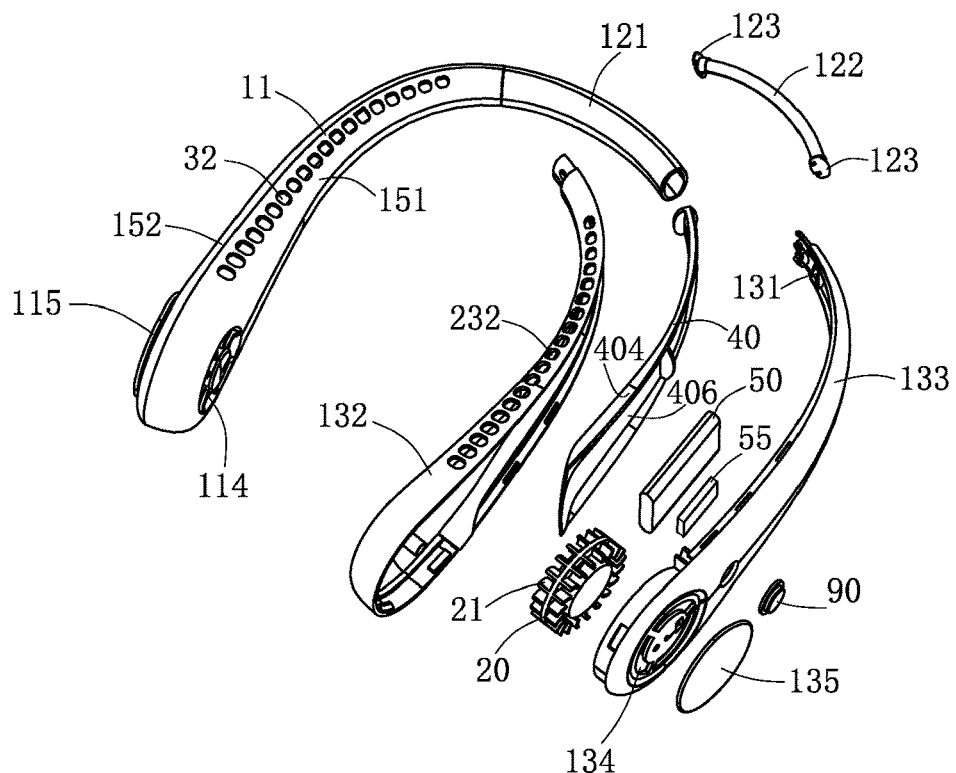
FIG. 3 is another partially exploded view of FIG. 1.
Figure 4:
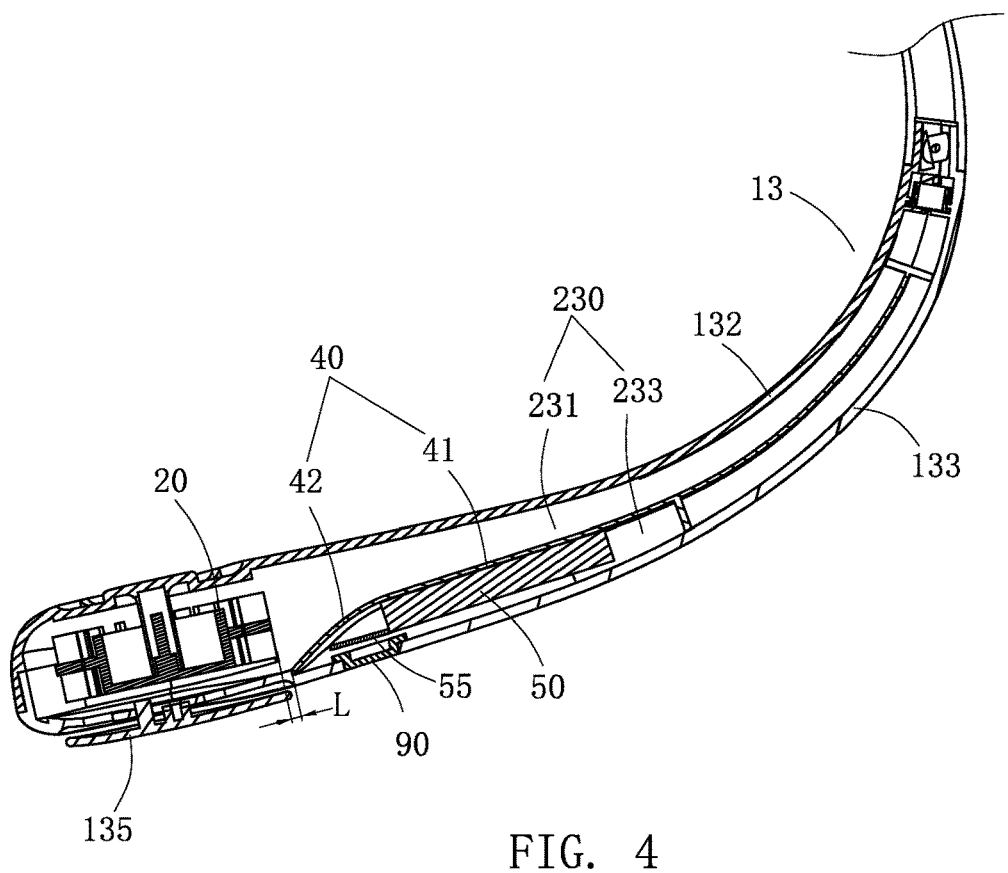
FIG. 4 is a sectional view of a first support of the portable blowing device of FIG. 1.

In order to further explain the technical means and efficacy adopted by the present disclosure to achieve the intended purpose of the present disclosure, the specific implementation mode, structure, characteristics and efficacy of a portable blowing device according to the present disclosure are described in detail as follows with reference to the attached drawings and preferred embodiments.

Embodiment 1

As shown in FIG. 1 to FIG. 4, a portable blowing device for example a neck fan in accordance with a first embodiment of the present disclosure comprises a body 10 for resting on the neck of a human body and fans 20 disposed in the body 10. Air channels 230 corresponding to the fans 20 are arranged in the body 10, and the air channels 230 extend along the length of the body 10 (i.e., a circumference of the neck), that is, the extending direction of the air channels 230 and the extending direction of the body 10 are the same. A wind shield 40 is arranged in the air channel 230. Preferably, a periphery of the wind shield 40 is closely connected with a part of a side wall of the air channel 230, so that a sub-air channel 231 is formed between the wind shield 40 and the other part of the side wall of the air channel 230. Air outlets 232 communicating with the outside are formed in the other part of the side wall of the air channel 230 corresponding to the sub-air channel 231. Airflow generated by the fan 20 is capable of entering the sub-air channel 231 and then exiting the sub-air channel 231 via the air outlets 232.

According to the neck fan provided in the present embodiment, the wind shield 40 is provided in the air channel 230 of the body 10 to form the sub-air channel 231 in the air channel 230. Airflow generated by the fans 20 enters the sub-air channels 231 and then exits the air outlets 232. Compared with the air channel 230, the sub-air channel 231 has a reduced cross section area and therefore a reduced volume. The airflow generated by the fans 20 is concentrated after entering the sub-air channel 231, and airflow blown out from the air outlets 232 is strengthened, so that the cooling effect and the user experience are improved.

Specifically, in the present embodiment, the wind shield 40 is an independent member arranged in the body 10. The body 10 comprises a first support 11, a second support 13 and a flexible connector 12 connecting the first support 11 with the second support 12. Each of the first support 11 and the second support 13 is provided with the air channel 230 and the wind shield 40 located in the air channel 230. The ends, away from the flexible connector 12, of the first support 11 and the second support 13 are respectively provided with the fans 20. The flexible connector 12 comprises a soft rubber sleeve 121 and a bending and shaping member 122 located in the soft rubber sleeve. Two opposite ends of the bending and shaping member 122 are respectively connected with locking members 123. The ends of the first support 11 and the second support 13 are respectively provided with locking grooves 111/131, and the locking members 123 are locked in the locking grooves 111/131, so that the flexible connector 12 connects the first support 11 with the second support 13 to form the whole body 10. It is understandable that the structure of the flexible connector 12 is not limited to the structure described in detail above, so long as it enable the body 10 be bent or straightened to enlarge or reduce the opening formed between the first and second supports 13. In the present embodiment, the body 10 is configured to comprise the flexible connector 12, the first support 11 and the second support 13, so that the body 10 can be bent, straightened or deformed at the flexible connector 12, which enables a user to bend, straightened or deform the body 10 to wear it on the neck easily. Specifically, in the present embodiment, the bending and shaping member 122 is a metal hose.

In other embodiments, if the body 10 has a large enough opening formed between the first and second supports 13 to allow the user to wear it, the body 10 may not comprise the flexible connector, that is, the flexible connector is omitted and the body 10 is formed as a one-piece component. Two ends of the one-piece body 10 are respectively provided with the fans 20, and the air channels 230 and the sub-air channels 231 corresponding to the fans 20 are arranged between the two fans 20. Alternatively, one or two fans 20 may be arranged in the middle of the body 10, and air channels 230 and sub-air channels 231 corresponding to the fans 20 are respectively arranged on both sides of the body 10.

Further, the first support 11 and the second support 13 respectively comprise first housings 112/132 and second housings 113/133, and the first housings 112/132 and the corresponding second housings 113/133 cooperatively form the air channels 230 after being assembled together. The fan 20 in the first support 11 is disposed at an end, away from the flexible connector 12, of the first support 11. The fan 20 in the second support 13 is disposed at an end, away from the flexible connector 12, of the second support 13. The air channels 230 of the first support 11 and the second support 13 are separated by the flexible connector 12.

The wind shield 40 comprises a shielding part 41 extending along the length direction of the corresponding air channel 230, and a connecting part 42 connected to one end of the shielding part 41 facing the corresponding fan. One end of the connecting part 42 is connected with the shielding part 41, and the other end abuts against the part of the side wall of the air channel 230, so that the sub-air channel 231 is formed between the wind shield 40 and the other part of the side wall of the air channel 230. Airflow generated by the fan 20 enters the sub-air channel 231 and then is blown to the outside from the air outlets 232. In the present embodiment, the wind shield 40 divides the corresponding air channel 230 into the corresponding sub-air channel 231 and a cavity 233 which does not communicate with the sub-air channel 231. Thus, the wind shield 40 can prevent the airflow generated by the fan 20 from entering the cavity 233. A battery 50 and a circuit board 55 electrically connected with the corresponding fan 20 are arranged in the cavity 233. The circuit board 55 is also electrically connected with a switch 90 which is arranged outside the body 10. The battery 50 is configured to supply power to the fan 20, and the switch 90 is configured to control the fan 20. Preferably, a surface, facing the sub-air channel 231, of the connecting part 42 is a smooth slope, such as a smooth straight surface or a smooth curved surface, so that the connecting part 42 has less resistance to the airflow generated by the fan 20 and allows the airflow to enter the sub-air channel 231 more easily. The battery 50 is located at a position, close to the connecting part 42, in the cavity 233 and contacts with the shielding part 41, so that heat generated by the battery 50 during operation can be transferred to the shielding part 41 and then be taken away by the airflow generated by the fan 20 to thereby prevent the battery 50 from overheating.

The fan 20 has a rotation center, and the fan 20 comprises a plurality of blades 21 arranged around the rotation center. The distance L between an end, close to the fan 20, of the wind shield 40 and a tangent line of a circular rotation track formed by the ends of the plurality of blades 21 is 2-7 mm. With this design, the airflow generated by the fan 20 can enter the sub-air channel 231 to the maximum extent, so that the utilization rate of the fan 20 is improved. In the present embodiment, the distance L is preferably 3-5 mm.

In the present embodiment, the body 10 is of an arc-shaped structure for fitting the neck of a user such as a human body. The body 10 comprises an inner side wall 151 close to the neck of the human body and an outer side wall 152 away from the neck of the human body in use, and the air outlets 232 penetrate through the inner side wall 151. In the present embodiment, the second housings 113/133 are formed as the outer side walls 152 of the supports. Thus, the second housings 113/133 is also named as outer housings. The first housings 112/132 are formed as the inner side walls 151 of the supports. Thus, the first housings 112/132 is also named as inner housings. The first housings 112/132 and the second housings 113/133 are respectively provided with air inlets 114/134 at positions corresponding to the fans 20, the second housings 133/133 are provided with protective covers 115/135 at positions corresponding to the air inlets 114/134, and the protective covers 115/135 cover the air inlets 114/134 of the second housings 113/133 and are spaced from the air inlets 114/134. This design can effectively prevent the user's hair from entering the fans 20 through the air inlets 114/134 of the second housings 113/133 when the user wears the neck fan. Due to the protective covers 115/135 are spaced from the air inlets 114/134 with gaps formed therebetween, the fans 20 can draw external airflow through the gaps to generate airflow.

In the present embodiment, there are a plurality of air outlets 232 which are formed in the inner side walls 151 of the supports 11/13 and arranged side by side at intervals along the length of the body 10, so that the airflow generated by the fans 20 can blow to most parts of the neck of the human body, allowing a larger cooling area and a better cooling effect. In the present embodiment, the wind shields 40 are plate-shaped, and peripheries of the wind shields 40 closely contact the inner surfaces of the second housings 113/133, i.e., the outer side walls 152, so that the air channels 230 are divided into the sub-air channels 231 located in the inner side and the cavities 233 located in the outer side. In the present embodiment, the upper and lower sides of the wind shield 40 are bent and extended toward the outer side wall to form hems 404, so that a groove 406 is formed between the two hems 404. The shape of the groove 406 matches the shape of the battery 50, and the battery 50 is at least partially located in the groove 406, so that the battery 50 can be better positioned and firmly located in the cavity 233. Of course, in other embodiments, the peripheries of the wind shields 40 may closely contact the inner side walls 151 and the outer side walls 152, so that the wind shields 40 form the cavities 233 with part of the inner side walls and the outer side walls, and the wind shields 40 form the sub-air channels 231 with the other part of the inner side walls and the outer side walls. The present disclosure does not limit which part of the side wall of the air channel 230 the wind shield 40 is connected with in the body 10. In other embodiments, the wind shield 40 can also be a rubber block with a certain thickness formed by integrally extending from the inner side surface of the first housing 112/132 or the second housing 113/133, or a rubber block with a certain thickness assembled in the air channel 230 and closely contacting with part of the side wall of the air channel 230. The specific shape and forming mode of the wind shield 40 are not limited in this present disclosure, as long as a sub-air channel 231 with a reduced cross section area can be formed in the air channel 230.

Embodiment 2

Figure 5:
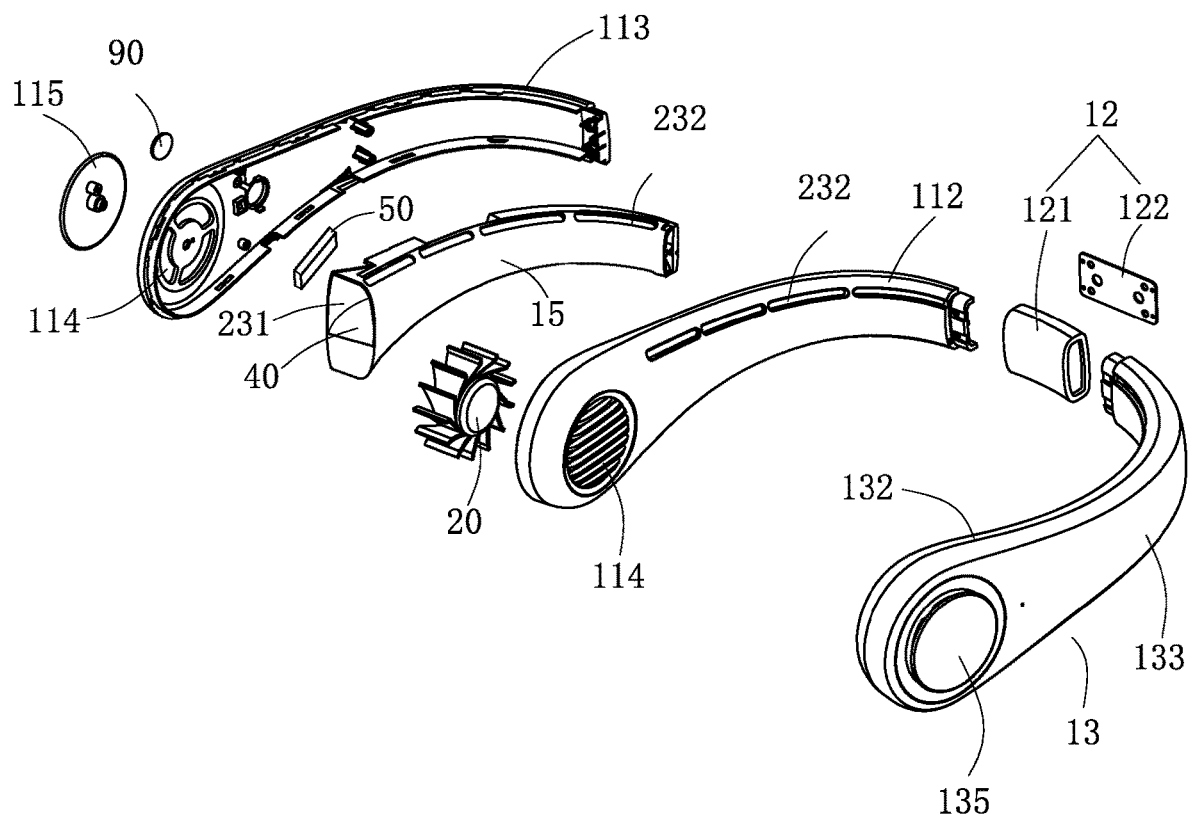
FIG. 5 is a perspective exploded view of a portable blowing device according to Embodiment 2 of the present disclosure.
Figure 6:
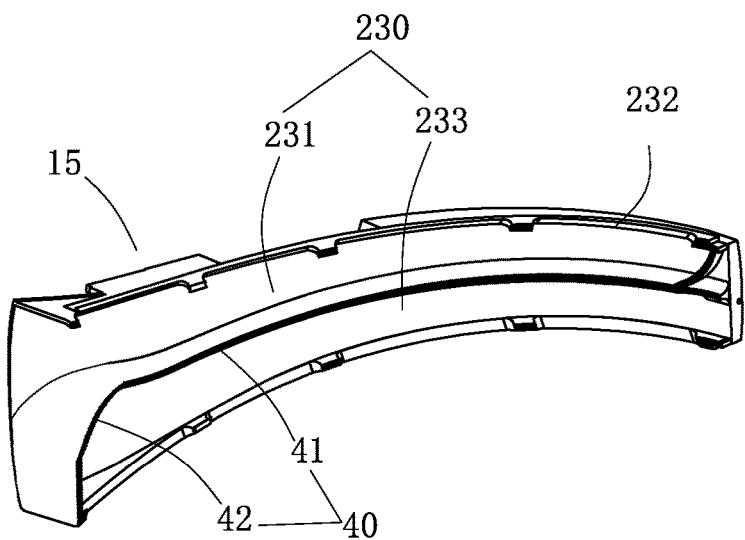
FIG. 6 is a sectional view of an inner case of the portable blowing device of FIG. 5.

The present embodiment is partially identical to Embodiment 1, and the same parts are not repeated here. The difference is as following: as shown in FIG. 5 and FIG. 6, the first housings 112/132 and the second housings 113/133 are connected to form cavities therebetween, and an inner case 15 hermetically connected with an inner surface of the cavity is arranged in the cavity, that is, an outer surface of the inner case 15 closely contacting with the inner surface of the cavity, the air channel 230 is arranged in the inner case 15, and the wind shield 40 is disposed in the air channel 230 of the inner case 15. By arranging the integrally formed inner case 15 with the air channel 230 formed therein, after the first housings 112/132 and the second housings 113/133 are assembled to form the cavities, the integrally formed inner case 15 is located in the cavity. Even if there are small gaps located at the joints between the first housings 112/132 and the second housings 113/133, the airflow generated by the fans 20 will not escape through the joints between the first housings 112/132 and the second housings 113/133, thus achieving a strengthened airflow and a fast cooling effect. Further, in a preferred solution, the inner case 15 is in the shape of a hollow tube, and the wind shield 40 is a sheet-like partition integrally formed in the inner case 15. The partition, i.e., the wind shield 40, comprises a shielding part 41 extending along the length of the air channel 230 in the inner case 15 and a connecting part 42 connected to an end, facing the fan 20, of the shielding part 41. One end of the connecting part 42 is connected with the shielding part 41, and the other end is connected with a part of the side wall of the air channel 230, so that the sub-air channel 231 is formed between the wind shield 40 and the other part of the side wall of the air channel. In the present embodiment, the wind shield 40 is a partition, a cavity 233 is formed between a side, opposite the sub-air channel 231, of the wind shield and the side wall of the air channel, and electronic components such as batteries 50 can be placed in the cavity 233. Of course, in other embodiments, the wind shield 40 can also be a rubber block with a certain thickness integrally extending from the inner side wall of the air channel 230, or a rubber block with a certain thickness assembled in the air channel 230 and attached to the part of the side wall of the air channel 230. The specific shape and forming mode of the wind shield 40 are not limited, as long as a sub-air channel 231 with a reduced cross section area can be formed in the air channel 230.

According to the neck fan provided in the present embodiment, the wind shield 40 is arranged in the air channel 230 of the body 10, that is, the wind shield 40 is arranged in the air channel 230 of the inner case 15 to form the sub-air channel 231 in the wind shields 40. Airflow generated by the fans 20 enters the sub-air channels 231 and then is blown out to the outside from the air outlets 232. Due to the sub-air channels 231 has a reduced cross-section area, the airflow generated by the fan 20 is concentrated after entering the sub-air channel 231, and airflow blown out from the air outlets 232 is strengthened, so that the cooling effect and the user experience are improved.

In addition, in the present embodiment, the bending and shaping member 122 of the flexible connector 12 is a metal sheet, screw holes are respectively formed in the two ends of the metal sheet, and the ends of the first support 11 and the second support 13 are locked and connected with the metal sheet by screws respectively, so that the first support 11 and the second support 13 are connected to the two ends of the flexible connector 12 to form the body 10 of the neck fan.

Embodiment 3

Figure 7:
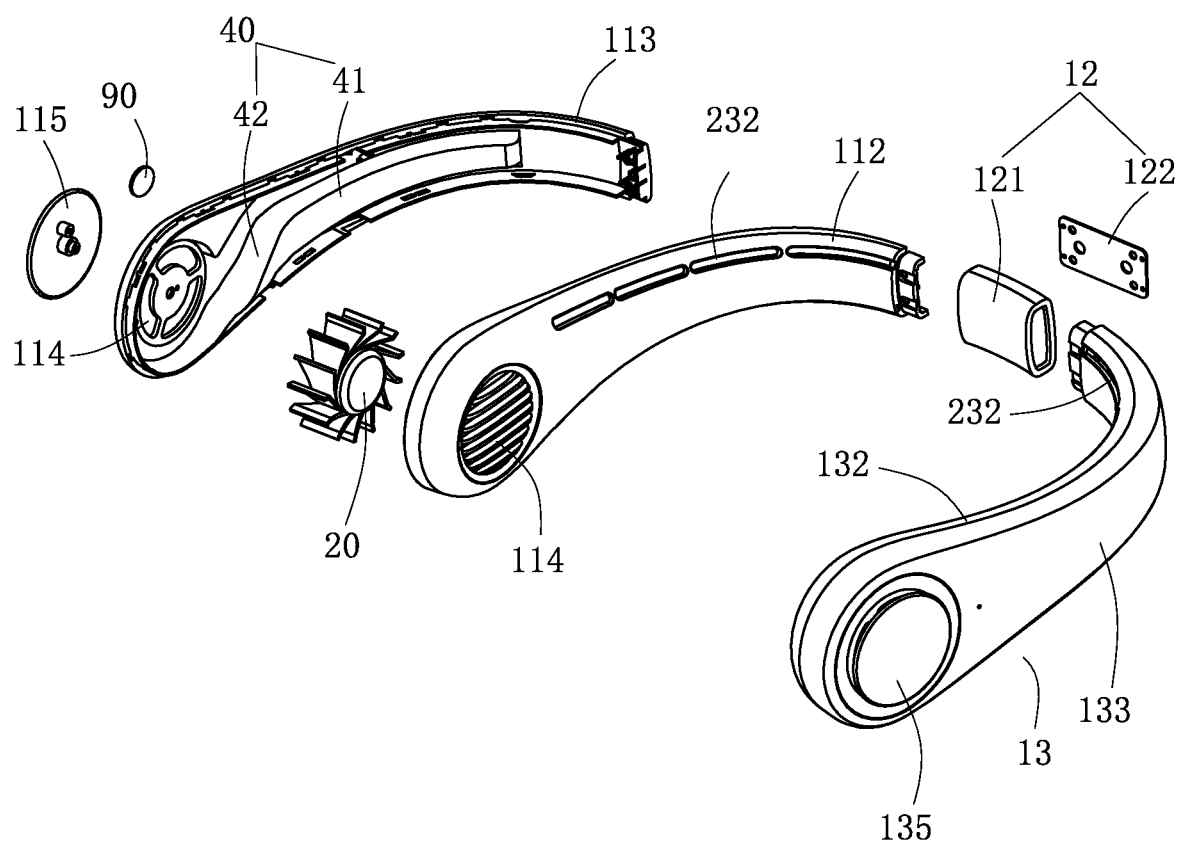
FIG. 7 is a perspective exploded view of a portable blowing device according to Embodiment 3 of the present disclosure.
Figure 8:
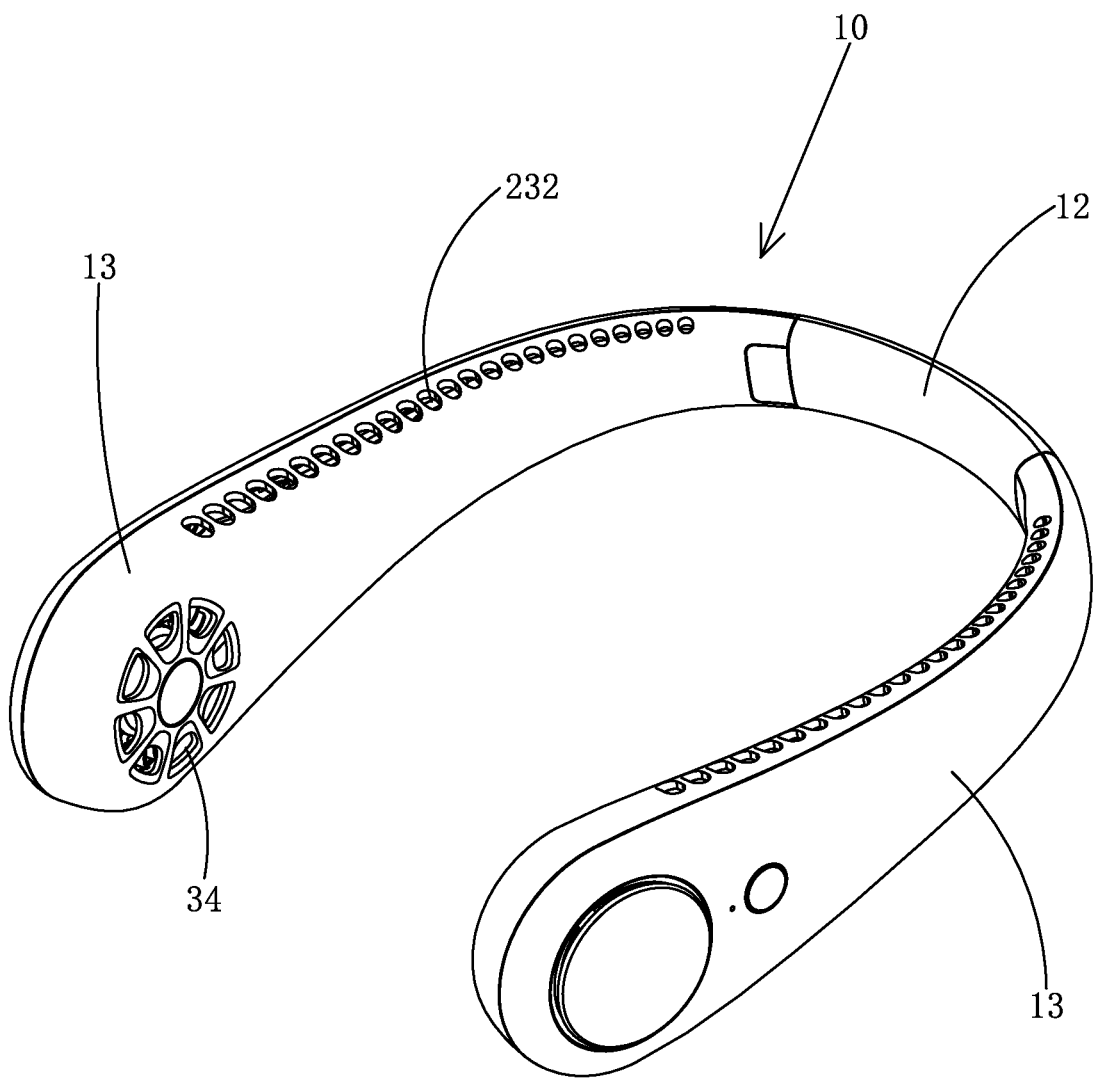
FIG. 8 is a perspective view of a portable blowing device according to the Embodiment 4 of the present disclosure.
Figure 9:
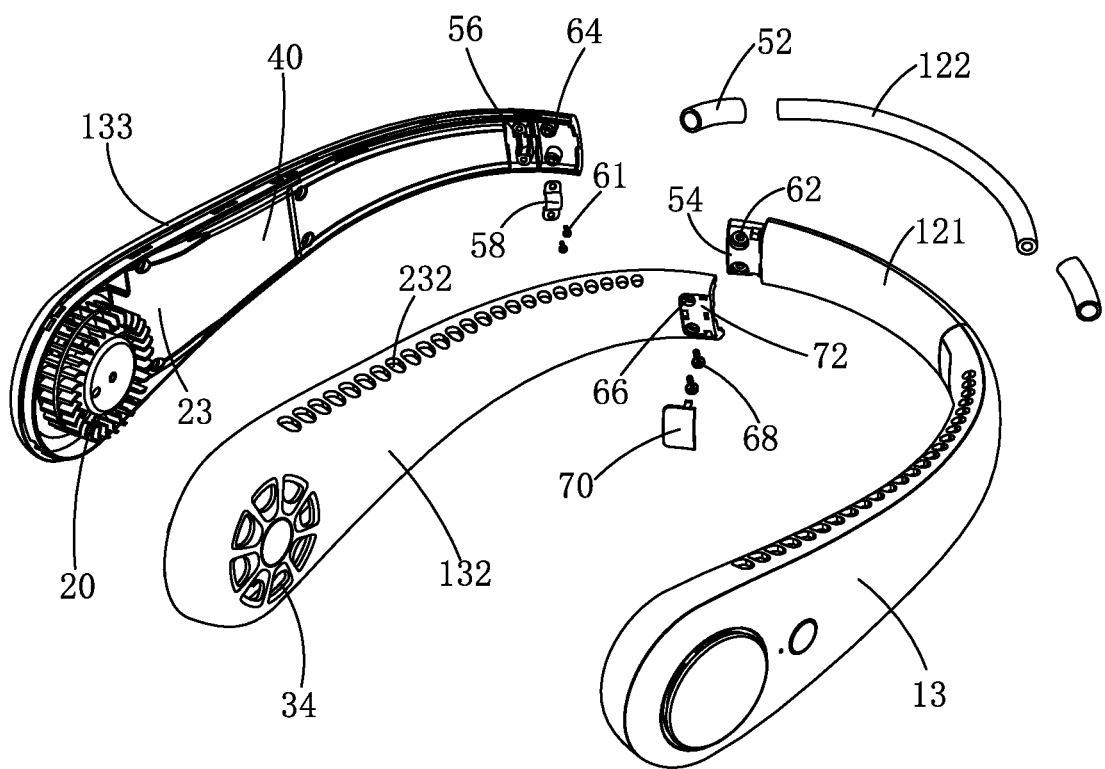
FIG. 9 is a partially exploded view of the portable blowing device in FIG. 8.
Figure 10:
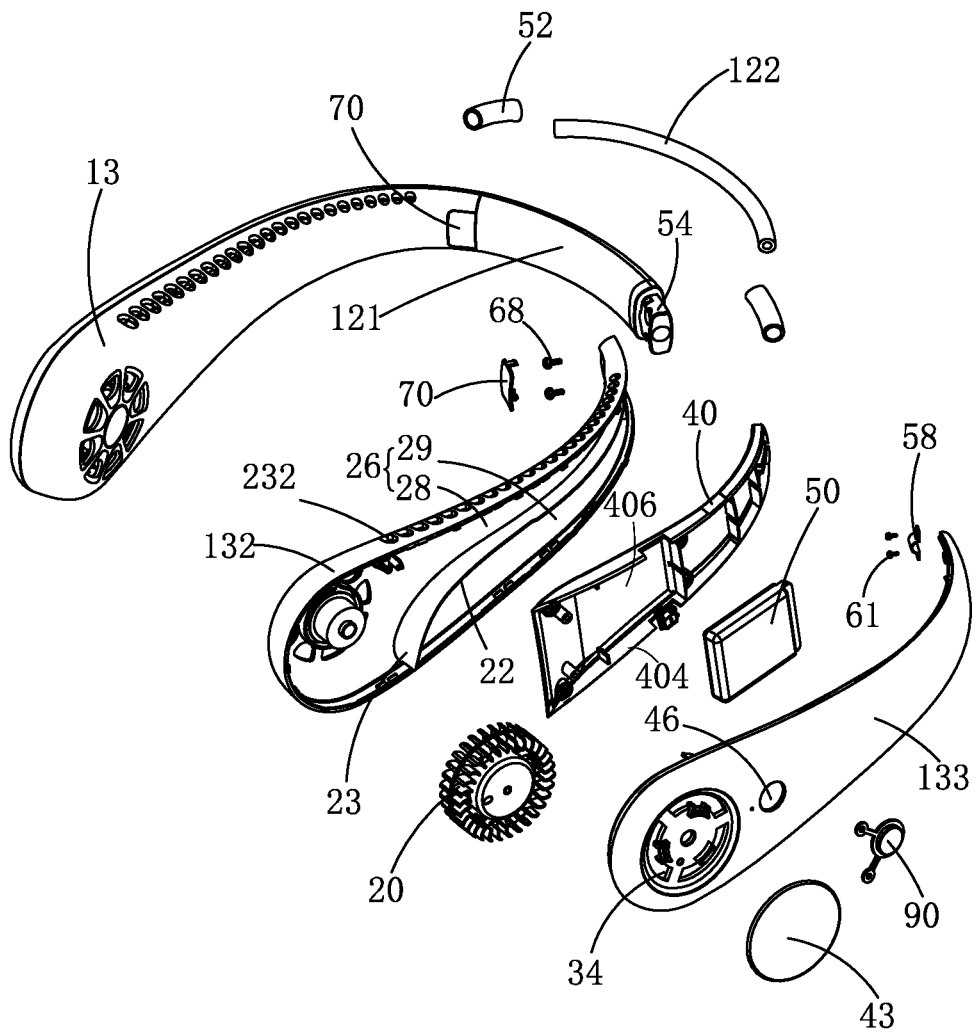
FIG. 10 is another partially exploded view of the portable blowing device in FIG. 8.
Figure 11:
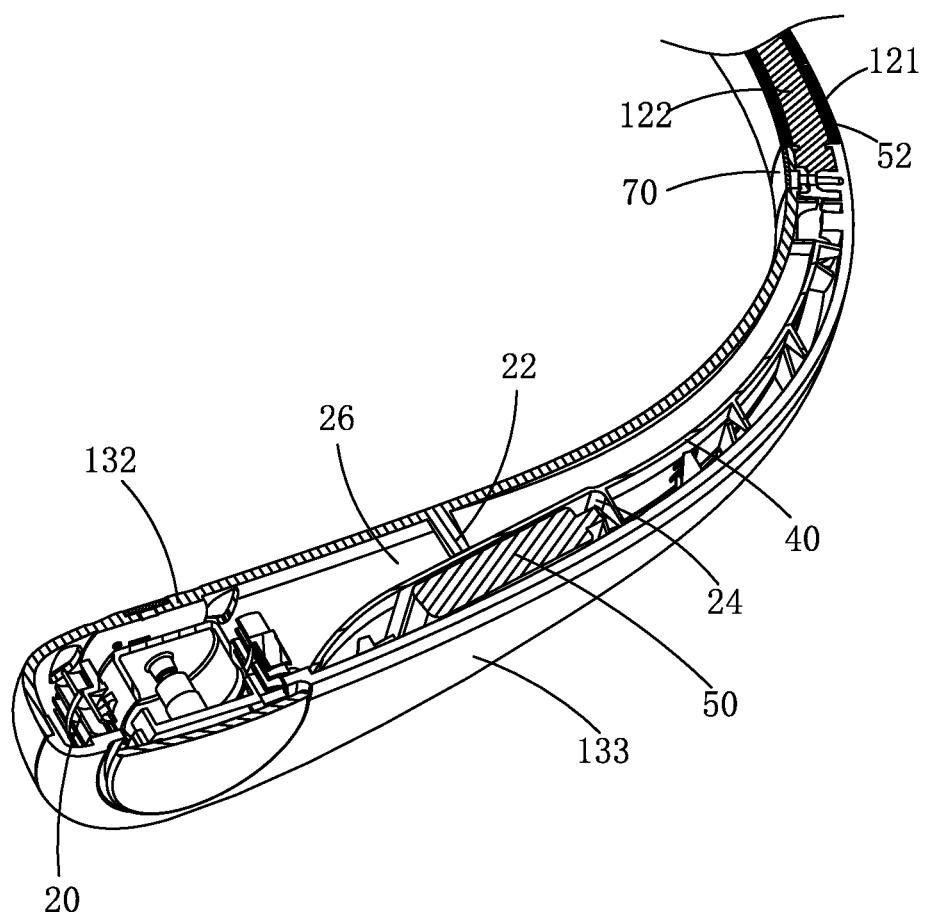
FIG. 11 is a partial structural sectional view of the portable blowing device in FIG. 8.

The present embodiment is partially identical to Embodiment 1, and the same parts are not repeated here. The difference is as following: as shown in FIG. 7, the wind shield 40 integrally extends from the inner surface of the second housing 113/133, that is, the outer side of the wind shield 40 is integrally connected with the inner surface of the second housing 113/133, and the inner side of the wind shield 40 closely contacts with the first housing 112/132 after the first housing 112/132 and the second housing 113/133 are assembled together, so that a sub-air channel 231 with a reduced cross-section area is formed in the air channel 230 which is formed by the assembled first housing 112/132 and second housing 113/133. In other embodiments, the wind shield 40 can also integrally extend from the inner surface of the first housing 112/132, that is, the inner side of the wind shield 40 is integrally formed with the inner side of the first housing 112/132, and the outer side of the wind shield 40 closely contacts with the second housing 133/133 after the first housing 112/132 and the second housing 113/133 are assembled together, so that a sub-air channel 231 with a reduced cross-section area is formed in the air channel 230 which is formed by the assembled first housing 112/132 and second housing 113/133. It is also possible that the wind shield 40 is formed by extension parts from both the first housing 112/132 and the second housing 113/133, that is, the first extension part extending from the first housing 112/132 form a first part of the wind shield 40 and the second extension part extending from the second housing 113/133 form a second part of the wind shield 40, and the first and second parts of the wind shield 40 cooperatively form the wind shield 40 after the first housing 112/132 and the second housing 133/133 are assembled together.

According to the neck fan provided in the present embodiment, the wind shield 40 is integrally formed in the air channels 230 of the supports, that is, the wind shield 40 integrally extends from the inner surface of the second housings 113/133, and the sub-air channel 231 with a reduced cross-section area is formed in the air channel 230 by the wind shield 40. Airflow generated by the fans 20 enter the sub-air channels 231 and then is blown out from the air outlets 232. Due to the sub-air channels 231 with reduced cross-section area, the airflow generated by the fans 20 is concentrated after entering the sub-air channels 231, and the airflow blown out from the air outlets 231 is strengthened, so that the cooling effect and the user experience are improved.

Embodiment 4

As shown in FIGS. 8-11, the present embodiment provides a portable blowing device, which is also a neck fan. The neck fan is to be put on the neck of the human body and comprises a body 10 and fans 20 arranged in the body 10. Cavities (i.e., air channels) corresponding to the fans 20 are formed in the body 10, wind shields 40 and partition members 22 are arranged in the air channels, and the wind shields 40 and the partition members 22 both extend along the length direction of the body 10. In the present embodiment, the body 10 comprises a flexible connector 12, two supports 13 respectively connected to two opposite ends of the flexible connector 12, and batteries 50 and circuit boards (not shown) arranged in the supports 13. There are two fans 20 which are arranged in the two supports 13 respectively, for example, at an end, away from the flexible connector 12, of the support 13. The fans 20 and the batteries 50 are electrically connected with the circuit boards to provide power to the fans 20. In the present embodiment, since the two supports 13 have the same structure and are symmetrically arranged, only one support 13 will be described below as an example.

In the present embodiment, the support 13 is of a hollow structure, the wind shield 40 is configured to divide the air channel in the support 13 into a first cavity 24 and a second cavity 26, and the partition member 22 is arranged in the second cavity 26 to further divide the second cavity 26 into a sub-air channel 28 and a sub-cavity 29. Preferably, the first cavity 24 and the sub-cavity 29 do not communicate with the sub-air channel 28, that is, the first cavity 24 and the sub-cavity 29 are both completely enclosed cavities, and airflow will not enter the first cavity 24 or the second sub-cavity 29 after entering the sub-air channel 28 which communicates with the corresponding fan 20. A side wall of the support 13 corresponding to the sub-air channel 28 is provided with air outlets 232 which communicate with the sub-air channel 28 and the outside of the support 13, the support 13 is provided with air inlets 34 corresponding to the fan 20, so that airflow generated by the fan 20 is blown out from the air outlets 232 after passing through the sub-air channel 28. Due to the dual separation of the air channel in the support 13 by the wind shield 40 and the partition member 22, the cross-section area of the sub-air channel 28 can be effectively reduced. In this way, the airflow generated by the fan 20 is concentrated after entering the sub-air channel 28, and the airflow blown out from the air outlets 232 is strengthened, so that the cooling effect and the user experience are improved.

In the present embodiment, the support 13 comprises a first housing 132 and a second housing 133 which are engaged together, and the air channel of the support 13 is formed between the first housing 132 and the second housing 133. Therefore, the outer side wall of the body 10 is the second housing 133 of the support 13, and the inner side wall of the body 10 is the first housing 132 of the support 13.

More specifically, the wind shield 40 is connected to an inner side of the outer side wall of the body 10, that is, connected to the inner side of the second housing 133, and the wind shield 40 extends along the length direction and width direction of the support 13, that is, the wind shield 40 has a length direction along the length direction of the support 13 and a width direction along the width direction of the support 13. The first cavity 24 is formed between an outer face of the wind shield 40 and the second housing 133, and the second cavity 26 is formed between an inner face of the wind shield 40 and the first housing 112, that is, the first cavity 24 and the second cavity 26 are distributed at intervals in the thickness direction of the support 13. The wind shield 40 is fixedly connected to the inner side of the second housing 133, for example, by interlocking means or screws. Opposite two sides of the partition member 22 are respectively connected with the inner side wall 132 of the support 13 and the inner face of the wind shield 40, and the partition member 22 has a plate/panel shape extending along the length direction and the thickness direction of the support 13, that is, the partition member 22 has a length direction along the length direction of the support 13 and has a width direction along the thickness direction of the support 13. In the present embodiment, one side of the partition member 22 is integrally connected to the inner surface of the first housing 132, and the other side of the partition member 22 closely contacts with the inner surface of the wind shield 40, so that the second cavity 26 is divided by the partition member 22 into the sub-air channel 28 and the second sub-cavity 29 distributed at intervals in the width direction of the support 13.

In the present embodiment, the air outlets 232 are arranged in an area between the fan 20 and the flexible connector 12 on the support 13. There is a plurality of air outlets 232 arranged along the inner side wall of the support 13, that is, extending along the length direction of the first housing 132. Specifically, the plurality of air outlets 232 are arranged on an upper side of the first housing 132 corresponding to the sub-air channel 28. In other embodiments, the air outlets 232 may also be arranged at other positions of the first housing 112 corresponding to the sub-air channel 28.

In the present embodiment, both the wind shield 40 and the partition member 22 are in the shape of arc panels adapted to the shape of the support 13 in the length direction of the support 13, and the ends, close to the fan 20, of the wind shield 40 and the partition member 22 are designed as smooth slopes 23, so that the airflow generated by the fan 20 can flow into the sub-air channel 28 more smoothly, effectively reducing the noise caused by the airflow hitting the partition member 22 and the wind shield 40. In the present embodiment, the partition member 22 acts as an air guiding member for guiding the airflow generated by the fan 20 into the sub-air channel 28.

The battery 50 and the circuit board can be arranged in the first cavity 24 or the sub-cavity 29, so that electronic components such as the battery 50 and the circuit board are separated from the sub-air channel 28, which avoids obstructing the airflow generated by the fan 20 and realizes a compact structure. In the illustrated embodiment, there are two batteries 50 which are respectively arranged in the first cavities 24 of the two supports 13, and the circuit board can be arranged in the first cavity 24 of one of the supports 13.

In the present embodiment, the air inlets 34 and the protective covers 43 are similar to that in Embodiment 1, which will not be repeated here.

In the present embodiment, a switch 90 is arranged on the outer side wall of the second housing 133, and the switch 90 is electrically connected with the circuit board and configured to control the start and stop of the fan 20. The switch 90 is a push-button switch, and an installation hole 46 is formed in the outer side wall of the second housing 133. The switch 90 is installed in the installation hole 46 and protrudes from the outer face of the second housing 133 for the user to press.

The flexible connector 12 comprises a bending and shaping member 122 and a soft rubber sleeve 121 covering the bending and shaping member 122. Two ends of the bending and shaping member 122 are respectively sleeved with metal sleeves 52 which are enclosed by the soft rubber sleeve 121. When the flexible connector 12 is connected with the support 13, a smooth transition is formed between an outer surface of the soft rubber sleeve 121 and an outer surface of the support 13. By sleeving the two ends of the bending and shaping member 122 with the metal sleeves 52 respectively, bending and deformation of the two ends of the flexible connector 12 can be effectively prevented, to thereby avoid gaps between the two ends of the flexible connector 12 and the supports 13 becoming larger.

The flexible connector 12 enables the orientation of the air outlets 232 of the neck fan 10 to be adjustable through bending and twisting the flexible connector 12, so that the airflow flowing out of the air outlets 232 can blow toward different parts of the human body such as the neck or the face of the human body. The bending and shaping member 122 can take and maintain any shape through bending and twisting, and the shape of the soft rubber sleeve 121 can be changed with the shape of the bending and shaping member 122. The bending and shaping member 122 can be a metal hose, a serpentine tube, a shaping steel wire, or other members made of a material making the flexible connector 12 have a shape memory function so that the flexible connector 12 can maintain its shape after being bent. The soft rubber sleeve 121 can be made of soft rubber such as TPU soft rubber.

The two ends of the flexible connector 12 are respectively locked and connected with the two supports 13. More specifically, two ends of the soft rubber sleeve 121 are respectively provided with connecting portions 54 for extending into connecting ends of the supports 13, the inner side wall of the second housing 133 is provided with a fixing base 56 which is provided with a screw hole. During assembly, an end of the bending and shaping member 122 extending out of the metal sleeve 52 and the connecting portion 54 penetrates into the connecting end of the support 13 and extends through the fixing piece 58 and is locked by the fixing base 56 and the fixing piece 58. The fixing piece 58 is of a fixing sheet structure which is arched toward one side to form a groove. Fixing holes are provided at opposite ends of the fixing piece 58. The fixing base 56 is provided with a recess corresponding to the end of the bending and shaping member 122. During installation, the fixing piece 58 is attached to the fixing base 56 with the groove of the fixing piece aligned with the recess of the fixing base 56 so that one side of the end of the bending and shaping member 122 is located in the recess of the fixing base 56, while the other side of the end of the bending and shaping member 122 is located in the groove of the fixing piece 58. The fixing piece 58 is fastened to the fixing base 56 by screws 61 passing through the fixing holes of the fixing piece 58 to be locked in the screw holes of the fixing base 56, thereby realizing the locking connection between the flexible connector 12 and the second housing 133.

Two positioning holes 62 are formed in the connecting portion 54, two positioning studs 64 are arranged on the inner side wall of the second housing 133 corresponding to the positioning holes 62, screw holes are formed in the positioning studs 64, and two through holes 66 are formed in the first housing 112 corresponding to the positioning holes 62. Screws 68 pass through the through holes 66 and the positioning holes 62 in sequence and then are engaged in the screw holes of the positioning studs 64, thus realizing the locking connection between the first support 11 and the flexible connector 12. In the illustrated embodiment, the neck fan 10 further comprises a snap cap 70. An area on the inner side wall of the first housing 112 corresponding to the through holes 66, for example, a connecting end of the first housing 112 is provided with a mounting groove 72. After being fastened in the through holes 66, heads of the screws 68 are located in the mounting groove 72, and the snap cap 70 is mounted to the mounting groove 72 in a snap fit mode to shield the screws 68 from being exposed, so that the appearance of the product is more attractive.

As described above, a locking connection is formed between the bending and shaping member 122 of the flexible connector 12 and the second housing 133 of the support 13 and another locking connection is formed between the first housing 132 of the support 13 and the soft rubber sleeve 121 of the flexible connector 12. That is, a double locking mechanism is formed between the flexible connector 12 and the support 13 which makes the connection between the flexible connector 12 and the support 13 more stable, thus making the structure of the neck fan stable and firm.

Embodiment 5

Figure 12:
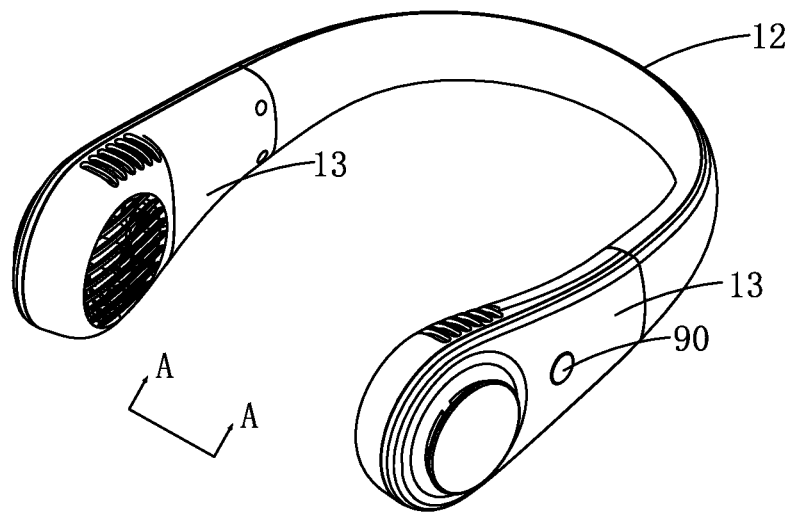
FIG. 12 is a perspective view of a portable blowing device according to Embodiment 5 of the present disclosure.
Figure 13:
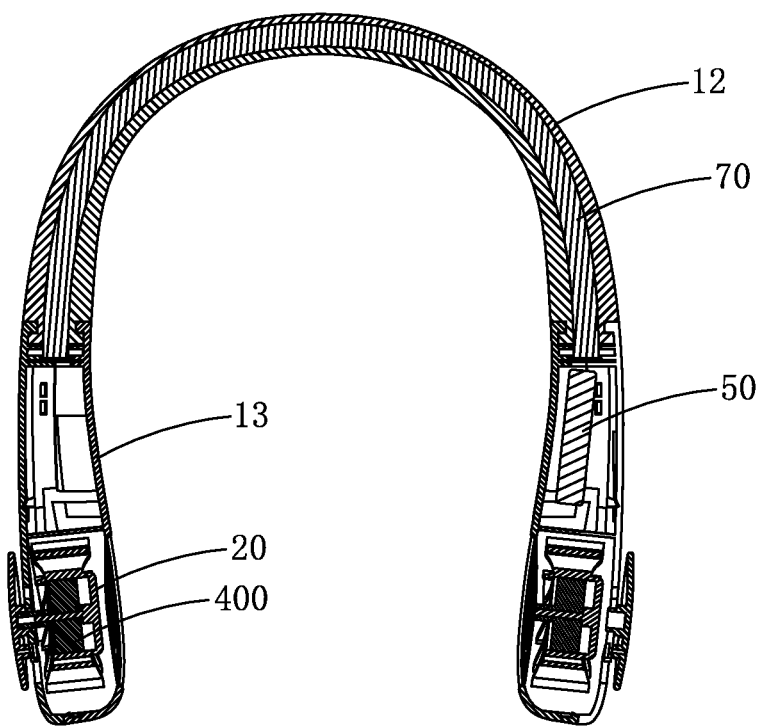
FIG. 13 is a cross-sectional view of the portable blowing device shown in FIG. 12 taken along A-A.
Figure 14:
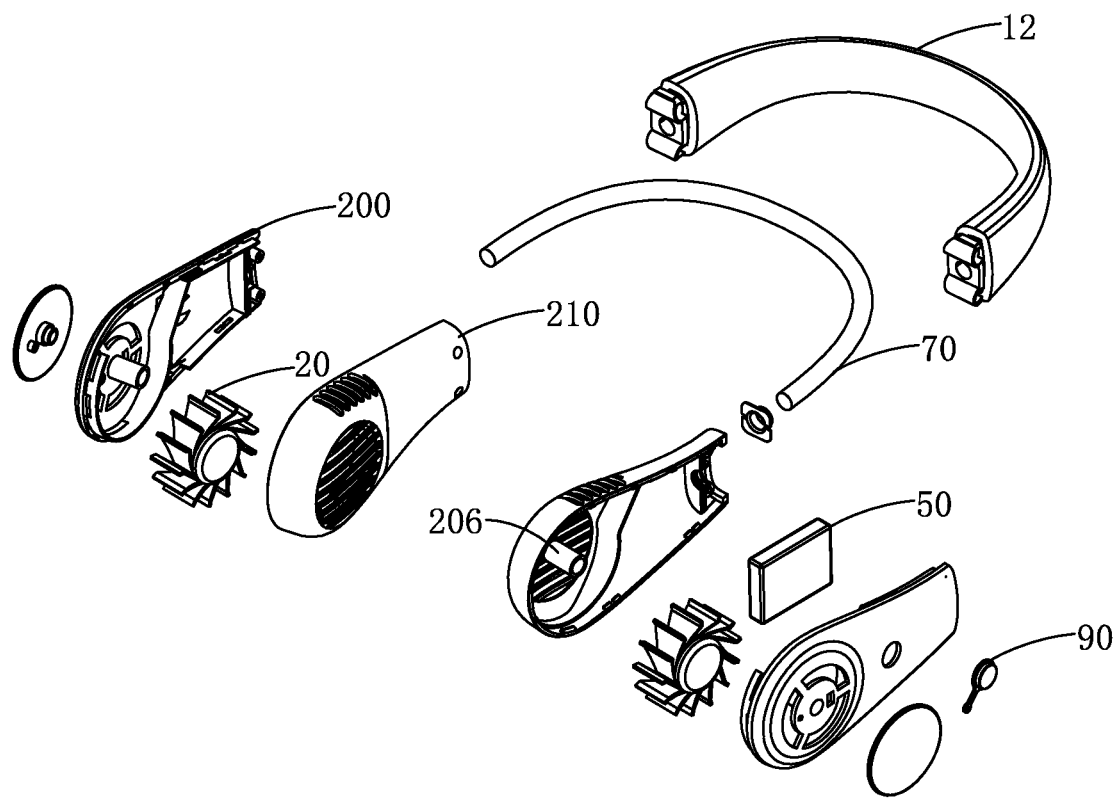
FIG. 14 is an exploded view of the portable blowing device shown in FIG. 12.

As shown in FIG. 12 to FIG. 14, a portable blowing device provided by the present embodiment is also a neck fan, which comprises an arc-shaped body for resting on the neck of the human body and fans 20 arranged in the body. The body comprises a connector 12 and supports 13 arranged at opposite two ends of the connector 12. Preferably, the connector 12 is an arc-shaped flexible connector 12. A fan 20 and a driving device 400 are arranged in each support 13, and each support 13 comprises an outer housing 200 (i.e., the outer side wall of the support 13) and an inner housing 210 (i.e., the inner side wall of the support 13), wherein the inner housing 210 is located on a side close to the neck of the human body and the outer housing 200 is located on a side away from the neck of the human body. Preferably, the driving device 400 in one support 13 is fixed on the outer housing 200, and the driving device 400 in the other support 13 is fixed on the inner housing 210. The driving device 400 is configured to drive the fan 20 to rotate.

In the neck fan of the above embodiment, the driving device 400 in one support 13 is fixed to the outer housing 200 while the driving device 400 in the other support 13 is fixed to the inner housing 210, and then the fans 20 are respectively connected with the driving devices 400, so that the left and right fans 20 have the same assembly direction when the neck fan is put on the neck of the human body, and the left and right fans 20 can be of the same type, which solves the problem that errors tend to occur during fan assembly and improves the universality of the fan. Because the left and right fans are exchangeable, the production cost is reduced, the assembly process is simplified, and the error rate is reduced.

Figure 15:
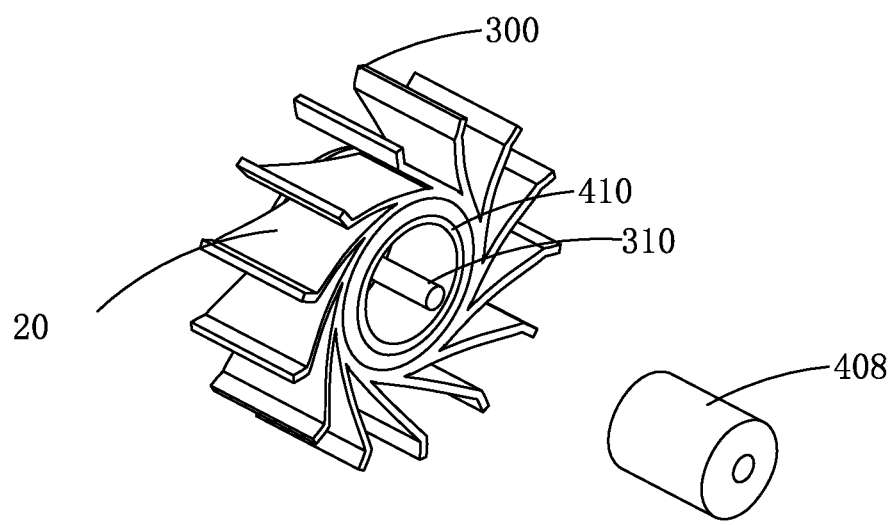
FIG. 15 is a structural diagram of a fan and a driving device of the portable blowing device shown in FIG. 14.

In one embodiment, as shown in FIG. 15, the driving device 400 comprises a stationary part 408 and a rotating part 410. The stationary part 408 of the driving device 400 in one support is fixed on the inner side wall of the outer housing 200, while the stationary part 408 of the driving device 400 in the other support is fixed on the inner side wall of the inner housing 210. The rotating part 410 is fixedly connected with the fan 20 so that the fan 20 is rotatable with the rotating part 410.

The stationary part 408 is provided with a through hole at its axial center. The fan 20 comprises an impeller 300 and a rotating shaft 310. The rotating shaft 310 is rotatably inserted into the through hole of the stationary part 408, so that the rotating part 410 is rotatable with respect to the stationary part 408 to thereby drive the impeller 300 to rotate. In other embodiments, a rod 206 is arranged on the inner surface of the outer housing 200 where the stationary part 408 is installed. The stationary part 408 is sleeved on the rod 206 and fixedly connected with the outer housing 200. The rod 206 is of a hollow structure. The rotating shaft 310 of the fan 20 is rotatably inserted into the rod 206, so that the stationary part 408 cooperates with the rotating part 410 to drive the impeller 300 to rotate about the axis of the rod 206.

Specifically, in the present embodiment, the driving device is described as a motor, and the stationary part 408 acts as a stator of the driving device 400. Each of the housings located at opposite ends of the arc-shaped body 10 is provided with a stator inside, one stator being fixed on the inner surface of the outer housing 200 and the other stator being fixed on the inner surface of the inner housing 210. The rotating part 410 acts as a rotor of the driving device 400. A chamber is formed around the rotating shaft 310 of the fan. The rotor is received in the chamber and tightly attached to an inner wall of the chamber. When the rotating shaft 310 is inserted into the through hole or the rod 206, the stator is located in the chamber and cooperates with the rotor to form the driving device 400. After being electrified, the rotor rotates to drive the fan impeller 300 to rotate.

In the above embodiment, the left and right fans can be assembled in the same direction, which solves the problem that the two fans are not exchangeable and assembly errors tend to occur in a traditional neck fan due to the left and right fans of the traditional neck fan are in a mirror-image relation.

In other embodiments, the driving device 400 comprises a motor (not shown). The motor in one support is fixed to the outer housing 200, and the motor in the other support is fixed to the inner housing 210. The fan 20 comprises an impeller 300 and a sleeve (not shown) which is sleeved on a bearing of the motor and fixedly connected with the bearing, so that the motor drives the impeller 300 to rotate.

Specifically, in the present embodiment, one end of the motor is fixed to the inner surface of the support 13, and the other end is provided with a rotatable bearing. Correspondingly, the fan 20 comprises an impeller 300 and a sleeve arranged at an axial center of the impeller. By the sleeve being sleeved on the bearing, the impeller 300 is connected to the bearing. When the motor works, the rotation of the bearing drives the impeller 300 to rotate, thus realizing the normal operation of the fan. In other embodiments, the fan comprises an impeller, and the axial center of the impeller is provided with a recess in which the bearing of the motor is fixedly received, so that the motor is capable of driving the impeller to rotate. Alternatively, the axial center of the impeller is provided with a through hole penetrating the impeller, and the bearing of the motor is inserted into the through hole and fixedly connected with the impeller, so that the motor drives the impeller to rotate. In other embodiments, the fixing method of the bearing of the motor and the impeller is not particularly limited.

Figure 16:
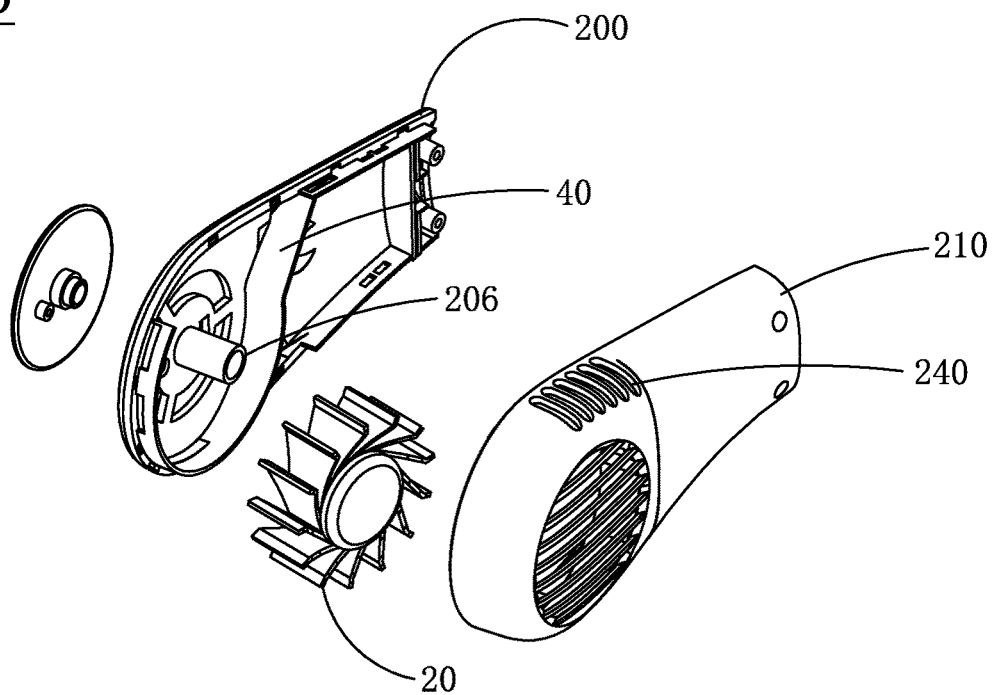
FIG. 16 is an exploded view of a support of the portable blowing device shown in FIG. 14.

In one embodiment, as shown in FIG. 16, the support 13 further comprises a wind shield 40 which is arranged within the support 13. Through holes 240, i.e., air outlets, are formed in a side face of the support 13 which is a face connected between an outer surface of the outer housing 200 and an outer surface of the inner housing 210. The wind shield 40 is configured for guiding the airflow generated by the fan 20 to the through holes 240 where the airflow exits the support 13.

Specifically, the outer housing 200 and the inner housing 210 of the support 13 are assembled to form therebetween a cavity (i.e., air channel) with one end open, the fan 20 and the driving device 400 are arranged in the cavity, and the open end of the support 13 is connected with the connector 12. Due to the connector 12 is hollow and the support 13 is long and thin, the airflow generated by the fan 20 tends to flow to the open end of the support 13 and not easily be led out of a housing 20 for cooling the user. By arranging the wind shield 40 in the support 13 and the through holes 240 in the side face of the support 13, after coming into contact with the wind shield 230, the airflow generated by the fan 20 flows along the wind shield 40 to the through holes 240, and then is led out of the housing 20 to achieve the effect of cooling. In the present embodiment, in order to achieve a good airflow guiding effect, the wind shield 40 is arc-shaped and extends from the side with the through holes of the support 13 to the other side of the support 13, so that when the outer housing 200 and the inner housing 210 are assembled, a sub-air channel communicating with the through holes 240 is formed by the wind shield 40 in the cavity (air channel) formed between the outer housing 200 and the inner housing 210, and the extending direction of the wind shield 40 is along the flow direction of the airflow, which makes the airflow generated by the fan 20 more concentrated after entering the sub-air channel and the airflow exiting the through holes 240 be strengthened. In other feasible embodiments, the wind shield 40 can be in other shapes, which is not particularly limited here.

In one embodiment, as shown in FIG. 14, the neck fan further comprises a bending and shaping member 70 which is a universal hose. The arc-shaped flexible connector 12 is made of a flexible material such as soft rubber, and the bending and shaping member 70 is arranged in the arc-shaped flexible connector 12. The bending and shaping member 70 is hollow and connecting wires such as leads can be arranged within the bending and shaping member 70. When the neck fan is used, the combined arc-shaped flexible connector 12 and universal hose 70 can be adjusted to any angle according to requirement of the user through bending and deforming. Meanwhile, the universal hose 70 ensures the stable connection of the leads.

Figure 17:
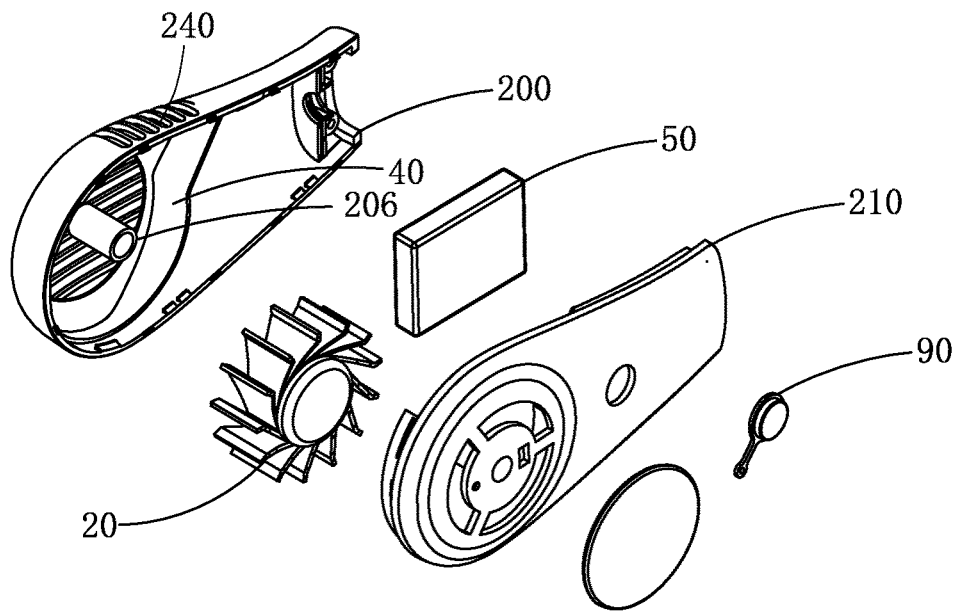
FIG. 17 is an exploded view of another support of the portable blowing device shown in FIG. 14.

In one embodiment, as shown in FIG. 17, the neck fan further comprises a switch 90 which is arranged on the support 13. In the present embodiment, a through hole corresponding to the switch 90 is defined in the outer housing 200 and the switch 90 is fixed in the through hole of the outer housing 200. By adjusting the switch 90, the start and stop of the neck fan can be realized. In addition, the wind power control of the neck fan can be realized by adjusting the switch 90.

Further, as shown in FIG. 17, the neck fan further comprises a battery 50, which is arranged in the support 13. In the present embodiment, it is assumed that the battery 50 is arranged in the support 13. By arranging the battery 50 in the support 13, when the fan 20 rotates, the battery 50 can provide power to the driving device 400, so that the neck fan can work at any time. In other embodiments, there may be two batteries 50, and each support 13 is provided with one battery 50 to provide power for the corresponding driving device 400, so that the neck fan has a longer endurance. Similarly, there may be two switches 90 which control the left and right driving devices 400 respectively, so that the driving devices 400 can work independently.

In the neck fan provided by the present embodiment, the driving device in one of the supports is fixed on the outer side wall while the driving device in the other support is fixed on the inner side wall, the left and right fans are assembled in the same direction, and the left and right fans can be of the same type, which solves the problem that errors tend to occur during fan assembly and improves the universality of the fan. Because the left and right fans are exchangeable, the production cost is reduced, the assembly process is simplified, and the error rate is reduced.

Embodiment 6

Figure 18:
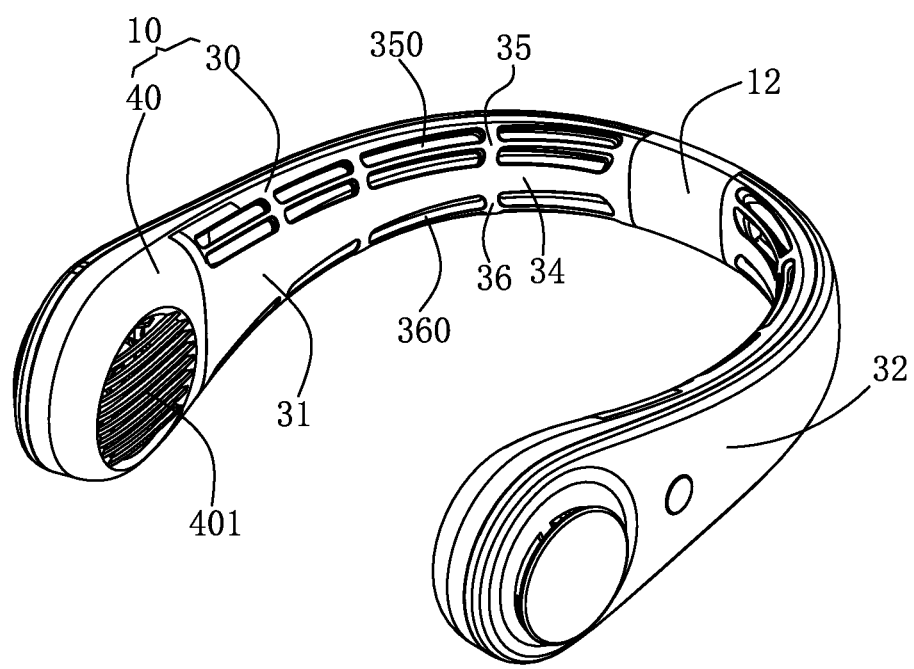
FIG. 18 is an assembled view of a portable blowing device according to Embodiment 6 of the present disclosure.
Figure 19:
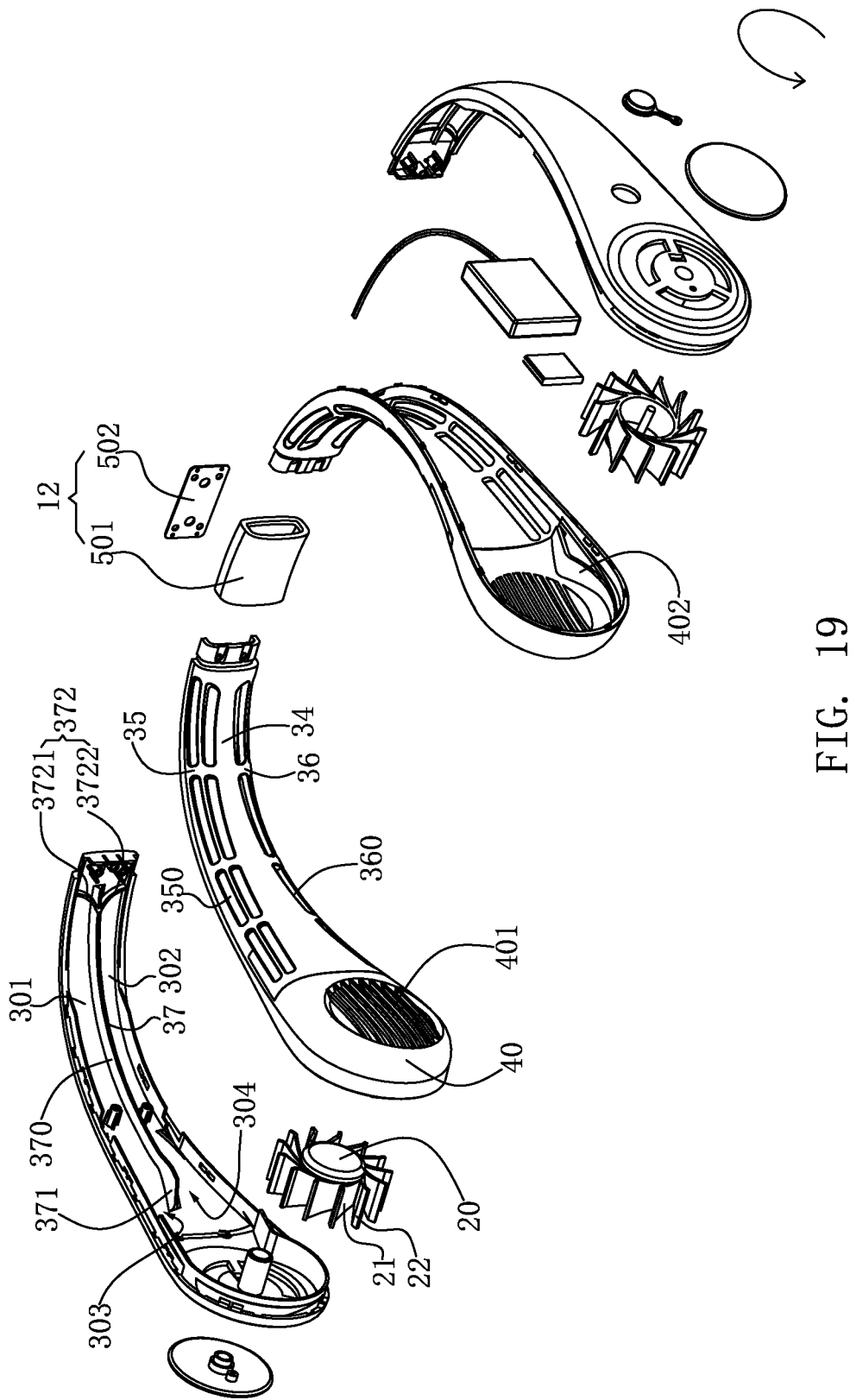
FIG. 19 is an exploded view of the portable blowing device in FIG. 18.
Figure 20:
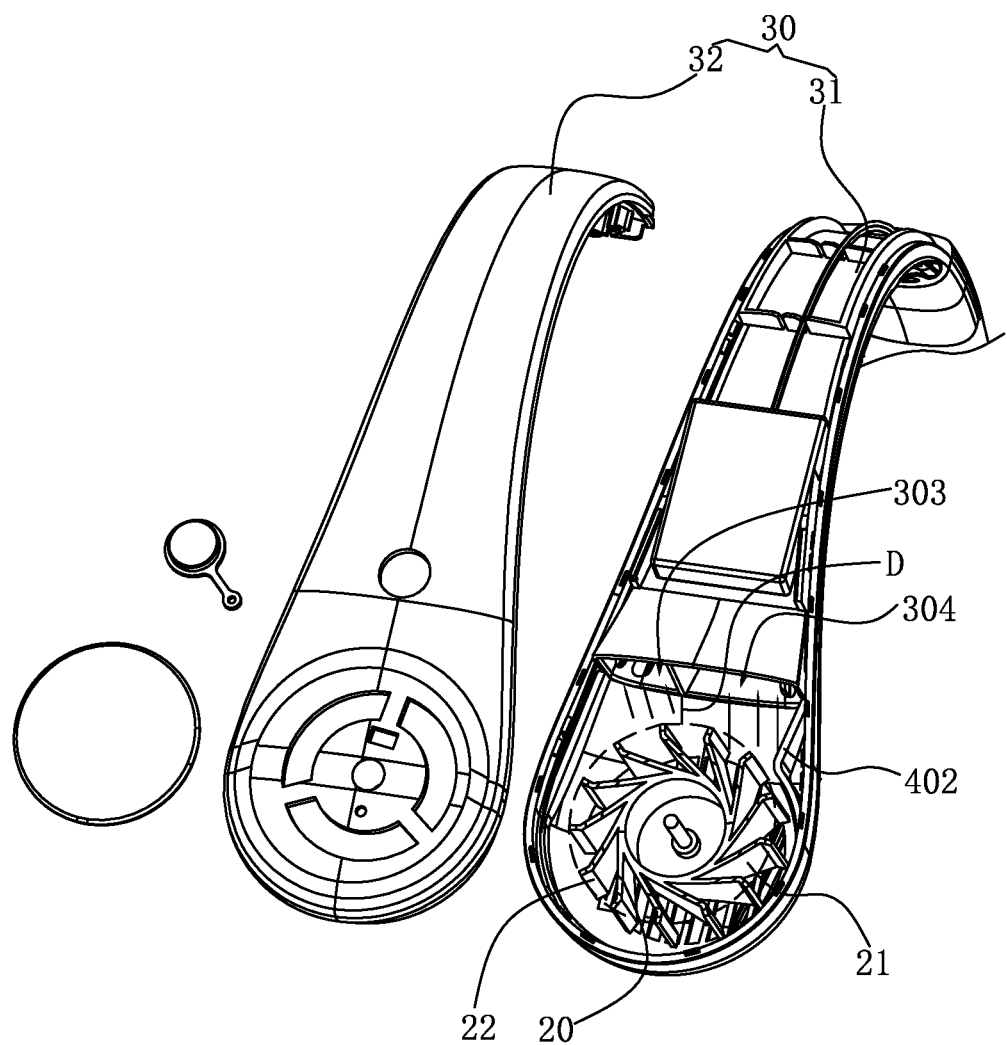
FIG. 20 is an exploded view of a support of the portable blowing device in FIG. 18, showing the placement of the fan.

As shown in FIGS. 18-20, a portable blowing device provided in the present embodiment is a neck fan which comprises a body 10 and fans 20 disposed in the body 10. The neck fan can be hung on the neck of the user through the body 10, so as to cool the user conveniently.

The body 10 comprises supports 30 and end housings 40 connected to ends of the supports 30.

As shown in FIGS. 18 and 20, the support 30 comprises an inner side wall 31 close to the neck of the user and an outer side wall 32 away from the neck of the user. The inner side wall 31 and the outer side wall 32 are detachably connected to ensure that a joint is airtight, or the inner side wall 31 and the outer side wall 32 can also be integrally formed by injection molding or other processes. In the present embodiment, outer surfaces of the inner side wall 31 and the outer side wall 32 are both curved smooth surfaces. The inner side wall 31 comprises a middle area 34 close to the neck of the user, and a first section 35 and a second section 36 located on the upper and lower sides of the middle area 34 respectively. The first section 35 is provided with first air outlets 350, and the second section 36 is provided with second air outlets 360. Of course, it can be understood that the outer surface of the inner side wall 31 can have three faces with certain angles formed therebetween or adjacent faces being perpendicular to each other, the first section 35, the middle area 34 and the second section 36 are located on the three faces respectively, and the axis of the first air outlets 350 arranged in the first section 35 and the axis of the second air outlets 360 arranged in the second section 36 are arranged at a certain angle (or in parallel).

As shown in FIG. 19, an air channel is arranged in the support 30. In the present embodiment, the support 30 is preferably in an arc shape, and an air guiding member 37 is arranged in the support 30. Specifically, in the present embodiment, the air guiding member 37 is in the shape of a strip and protrudes from an inner surface of the outer side wall 32, and the air guiding member 37 extends along the bending direction of the support 30. A top surface of the air guiding member 37 (i.e., the top surface in the protruding direction) contacts with the inner surface of the inner side wall 31 (i.e., the surface of the inner side wall 31 close the air channel) and the shapes of the top surface of the air guiding member 37 and the inner surface of the inner side wall 31 completely match at the joint to ensure airtightness of the joint between the top surface of the air guiding member 37 and the inner surface of the inner side wall 31. The air guiding member 37 divides the air channel into a first air channel 301 and a second air channel 302, the first air channel 301 communicates with the first air outlets 350, and the second air channel 302 communicates with the second air outlets 360. In other embodiments, the air guiding member 37 may be omitted and only one air channel is provided in the support 30, and the inner side wall 31 and the outer side wall 32 form a cavity acting as the air channel.

The airflow generated by the fan 20 passes through the air channel and blows toward the neck of the user at multiple angles through the first air outlets 350 and the second air outlets 360, so as to achieve an improved cooling effect.

Refer to FIG. 19, the inner side wall 31 and the outer side wall 32 of the support 30 can be connected by a detachable connecting structure, the upper and lower sides of the inner side wall 31 are respectively connected with the upper and lower sides of the outer side wall 32, one side of the air guiding member 37 is integrally formed with the inner surface of the inner side wall 31, and the other side of the air guiding member 37 abuts against an inner surface of the outer side wall 32. Alternatively, one side of the air guiding member 37 is integrally formed with the inner surface of the outer side wall 32, and the other side of the air guiding member 37 abuts against the inner surface of the inner side wall 31.

With reference to FIG. 18 and FIG. 19, in the present embodiment, there may be a plurality of first air outlets 350 and a plurality of second air outlets 360, and the plurality of first air outlets 350 and the plurality of second air outlets 360 in the same shape are arranged at equal intervals in the bending direction of the support 30.

As shown in FIGS. 19 and 20, in the present embodiment, the fan 20 is disposed in the end housing 40. The end housing 40 is provided with an air inlet 401, and the air inlet 401 can be of a grid structure. The end housing 40 is of an approximately circular structure which has a housing center (not labeled). The fan 20 has a rotation center (not labeled), and the rotation center of the fan and the housing center are eccentrically arranged. The fan 20 comprises a plurality of blades 21 arranged around the rotation center, a tail end of each blade 21 is provided with a deflection part 22 facing the air channel, and the deflection directions and deflection angles of the plurality of deflection parts 22 are the same, so as to guide the airflow toward the air channel. In the present embodiment, preferably, the tail ends of the plurality of blades 21 rotate around the rotation center to form a circular rotation track, and the perpendicular distance D from a starting end of the air guiding member 37 to the tangent of the circular rotation track is 2-7 mm. In a preferred solution, the perpendicular distance D from the starting end of the air guiding member 37 to the tangent of the circular rotation track can be 3-5 mm, so that the airflow generated by the fan 20 enters the first air channel 301 and the second air channel 302 sufficiently, so that the airflow blown out from the first air outlets 350 and the second air outlets 360 is strengthened.

With reference to FIG. 19 and FIG. 20, a guiding plate 402 is arranged in the end housing 40. Preferably, the guiding plate 402 is arranged around a periphery of the fan 20. The shape of the guiding plate 402 is preferably in accordance with the Archimedes spiral of a centrifugal fan, so as to guide more airflow into the air channel. Preferably, the guiding plate 402 is disposed on an inner surface of the end housing 40. The guiding plate 402 is integrally formed or detachably connected with the end housing 40.

In other embodiments, the fan 20 can also be arranged in the support 30, for example: arranged in the middle of the support 30, or arranged at the joint of the two supports 30.

As shown in FIGS. 19 and 20, in the present embodiment, the air guiding member 37 comprises a body part 370 protruding from the inner surface of the outer side wall 32. An end close to the fan 20 is defined as a starting end, and an end away from the fan 20 is defined as a tail end. Preferably, the curvature (or radian) of the body part 370 extended between the starting end and the tail end is the same as that of the support 30 A guide plate 371 is provided at the starting end of the body part 370, and the guide plate 371 is offset from the extending direction of the body part 370. That is, the guide plate 371 is of an inclined plate structure extending inclinedly from the starting end of the body part 370. The guide plate 371 comprises a tail end connected with the starting end of the body part 370 and a starting end away from the starting end of the body part 370. The starting end of the guide plate 371 is closer to the upper side of the outer side wall 32 than the tail end of the guide plate 371. Therefore, the starting end of the guide plate 371 divides an inlet of the air channel into a first air inlet 303 and a second air inlet 304, the first air inlet 303 corresponds to the first air channel 301, and the second air inlet 304 corresponds to the second air channel 302, that is, the first air inlet 303 and the second air inlet 304 communicate with the first air channel 301 and the second air channel 302 respectively. The cross-sectional area of the first air inlet 303 is smaller than that of the second air inlet 304. In a preferred solution, the cross-sectional area of the first air inlet 303 is half of that of the second air inlet 304, and the volume of airflow entering the first air channel 301 and the volume of air entering the second air channel 302 are substantially the same. Due to the arrangement of the guide plate 371, part of the airflow blowing toward the first air inlet 303 is diverted to the second air inlet 304, so that the airflow entering the first air channel 301 and the second air channel 302 is more uniform, which allows the first air outlet 350 and the second air outlet 360 to discharge airflow uniformly, thus avoiding the discomfort caused by uneven air discharge from upper and lower sides of the support 13.

The air guiding member 37 further comprises a wind shield 372 connected to the tail end of the body part 370, and the wind shield 372 stops at a tail end of the air channel. In the present embodiment, specifically, a first wind shield 3721 and a second wind shield 3722 are provided at the tail end of the body part 370. Two ends of the first wind shield 3721 are respectively connected with an upper inner surface of the outer side wall 32 and the body part 370 to stop the tail end of the first air channel 301, so that the airflow flows out of the first air outlets 350 after passing through the first air channel 301. Two ends of the second wind shield 3722 are connected with a lower inner surface of the outer side wall 32 and the body part 370 respectively to stop the tail end of the second air channel 302, so that the airflow flows out of the second air outlets 360 after passing through the second air channel 302 and finally reaches the neck of the user for cooling. As shown in FIGS. 19 and 20, in the present embodiment, the support 30 is of a minor arc structure, and the neck fan comprises two supports 30 of a minor arc structure. The body 10 of the neck fan further comprises a flexible connector 12, and the two supports 30 are connected by the flexible connector 12. Preferably, the two supports 30 are symmetrically arranged with respect to the flexible connector 12, and when the neck fan is put on the neck of the user, the two supports 30 are respectively located on the left and right sides of the neck of the user. The flexible connector 12 comprises a soft rubber part 501 and a metal piece 502 connected with the soft rubber part 501, and opposite ends of the metal piece 502 are respectively connected with the two supports 30. In the present embodiment, it is preferable to connect the metal piece 502 with the two supports 30 first, and then wrap the metal piece 502 with the soft rubber part 501 through an injection molding process, so that the flexible connector 12 is elastically deformable to allow the user to stretch the two supports to put on the neck fan easily, and the strength of the flexible connector 12 can be increased so that the flexible connector 12 can be repeatedly stretched and restored to the original state. In the present embodiment, the soft rubber part 501 is preferably made of a thermoplastic material with elastic deformation such as silica gel. The metal piece 502 is made of sheet-like metal with elastic deformation. Besides being arranged in the soft rubber part 501 through injection molding, the sheet-like metal piece 502 can be attached to the outside of the soft rubber part 501 by other means. In other embodiments, the metal piece 502 can also be a metal hose structure, which is not limited here.

Embodiment 7

Figure 21:
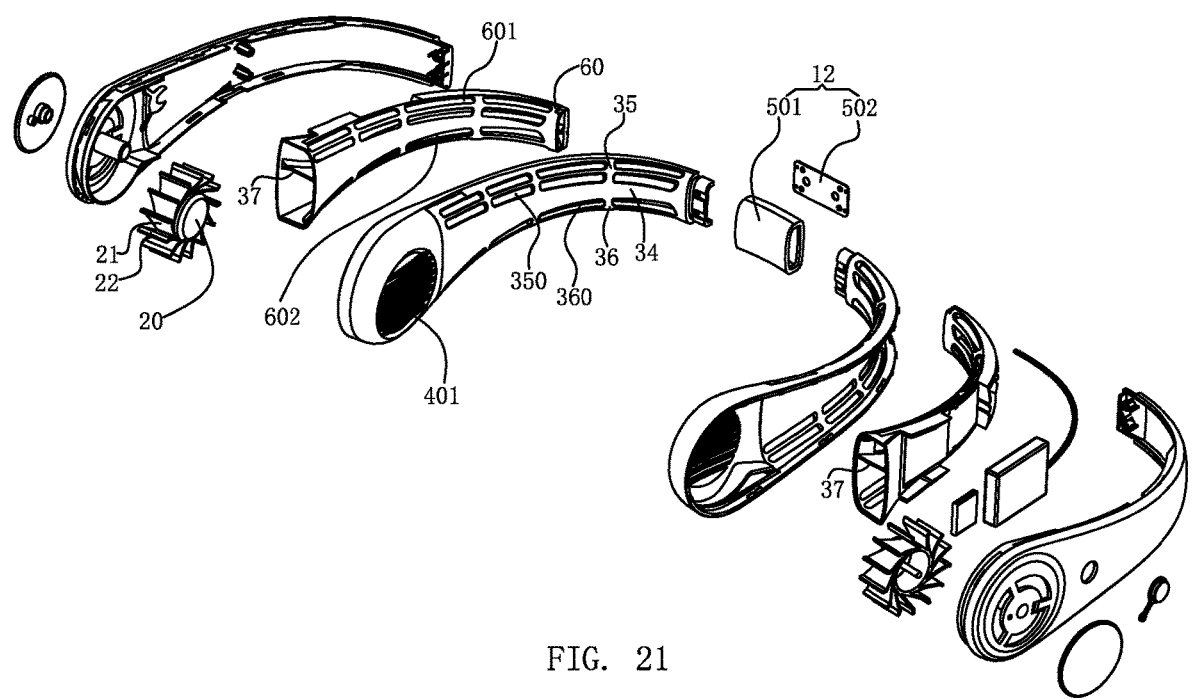
FIG. 21 is an exploded view of a portable blowing device according to Embodiment 7 of the present disclosure.
Figure 22:
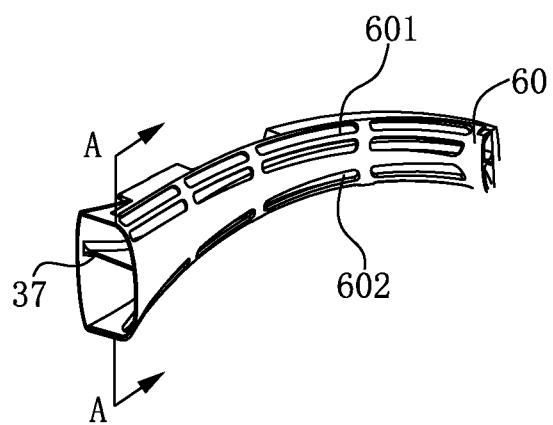
FIG. 22 is a view of an inner case of the portable blowing device according to Embodiment 7 of the present disclosure.
Figure 23:
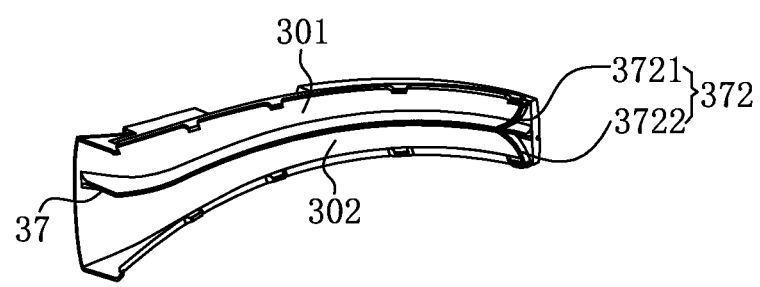
FIG. 23 is a sectional view of FIG. 22 taken along A-A.

The present embodiment is basically the same as Embodiment 6, and the same parts are not repeated here. The difference lies in that: as shown in FIGS. 21-23, the support 30 is further provided with an inner case 60 inside, and the inner case 60 is integrally formed and provided with an air channel inside. After the inner side wall 31 and the outer side wall 32 of the support 30 are assembled, the integrally formed inner case 60 is located in the cavity enclosed by the inner side wall 31 and the outer side wall 32. Even if there is a small gap at the joint between the inner side wall 31 and the outer side wall 32, the airflow will not escape through the joint between the inner side wall 31 and the outer side wall 32, whereby a strengthened airflow with a large volume can be output from the air outlets to cool the user fast. Further, in a preferred solution, the outer surface of the inner case 60 and the inner surface of the support 30 contact with each other and are matched in shape. The inner case 60 is provided with an air guiding member 37 inside, and the air guiding member 37 has a structure similar to that of the air guiding member 37 of Embodiment 6. The air guiding member 37 divides the air channel into a first air channel 301 and a second air channel 302. The inner case 60 is provided with first air vents 601 and second air vents 602. The first air channel 301 communicates with the first outlets 350 through the first air vents 601, and the second air channel 302 communicates with the second outlets 360 through the second air vents 602.

Embodiment 8

Figure 24:
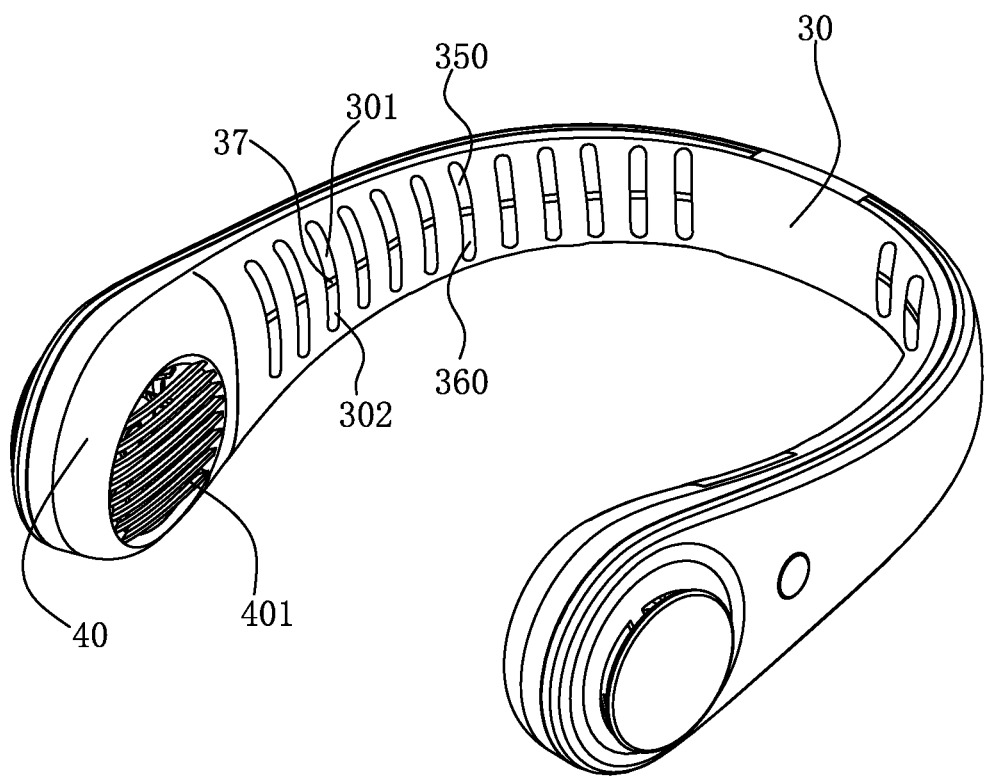
FIG. 24 is a perspective view of a portable blowing device according to Embodiment 8 of the present disclosure.
Figure 25:
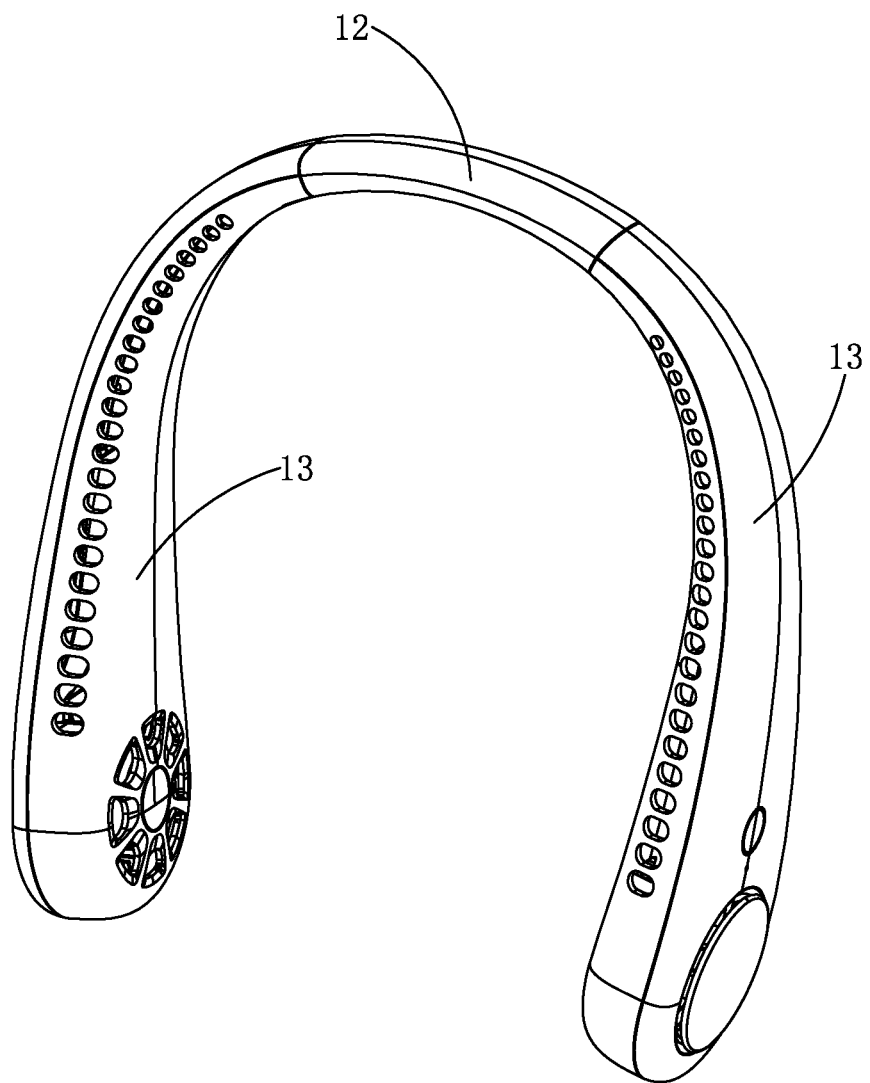
FIG. 25 is a perspective view of a portable blowing device according to Embodiment 9 of the present disclosure.
Figure 26:
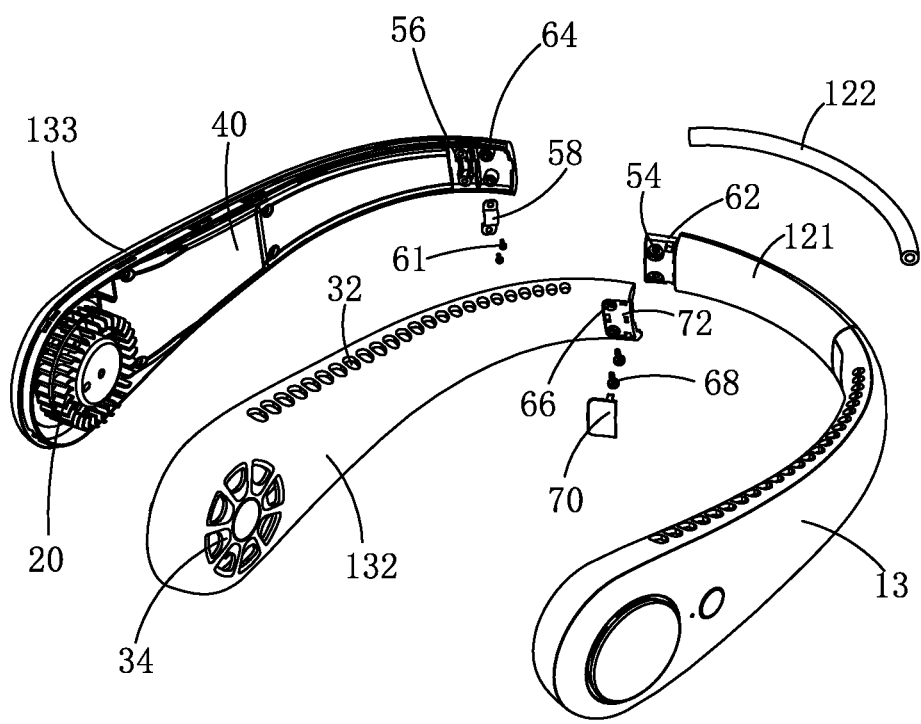
FIG. 26 is an exploded view of the portable blowing device in FIG. 25.
Figure 27:
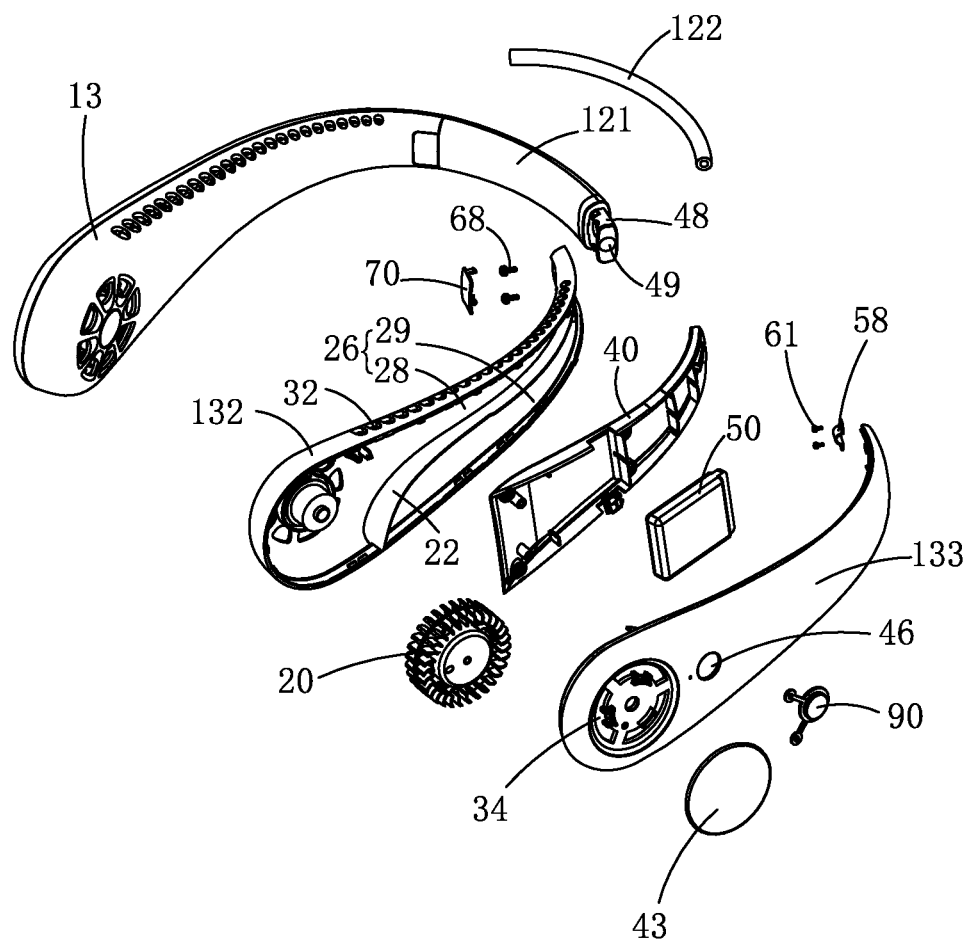
FIG. 27 is another exploded view of the portable blowing device in FIG. 25.

The present embodiment is partially identical to Embodiment 6, and the same parts are not repeated here. The difference lies in that: as shown in FIG. 24, the flexible connector 12 is omitted, and the support 30 can be an integral structure. In the present embodiment, the support 30 is of a major arc configuration, and the support 30 itself can be made of a material with elastic restoring force, so that the support 30 can be stretched by holding its two ends to be put on.

Embodiment 9

Figure 28:
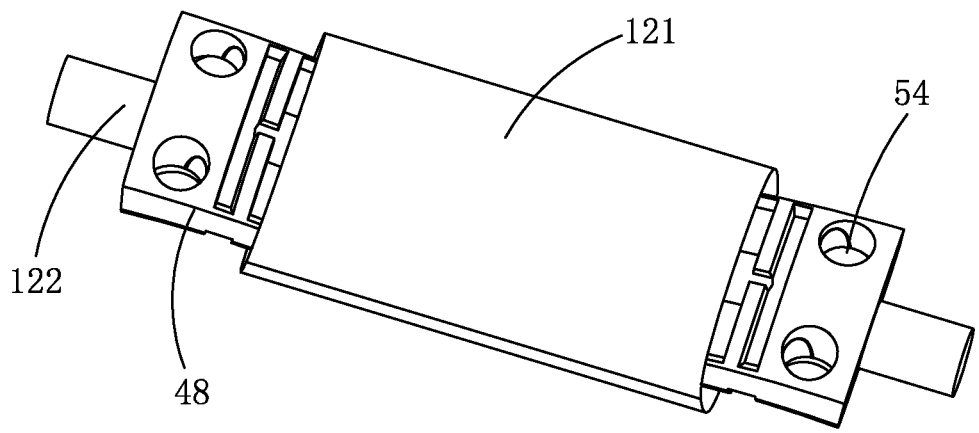
FIG. 28 is a perspective view of a flexible connection structure of the portable blowing device in FIG. 25.
Figure 29:
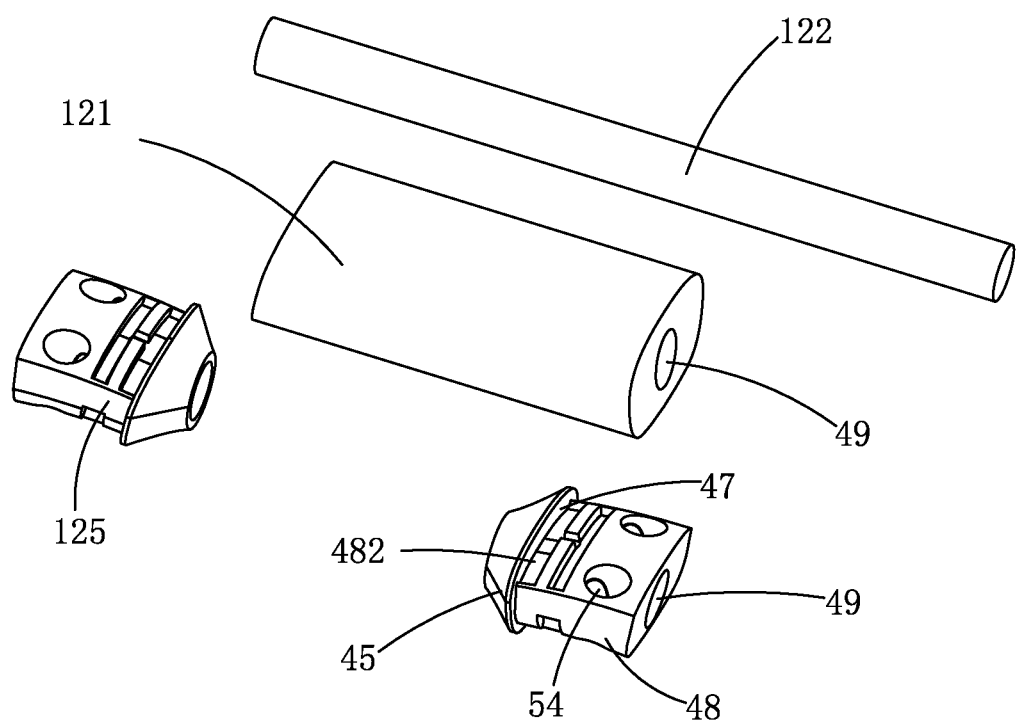
FIG. 29 is an exploded view of the flexible connection structure in FIG. 28 before injection molding.
Figure 30:
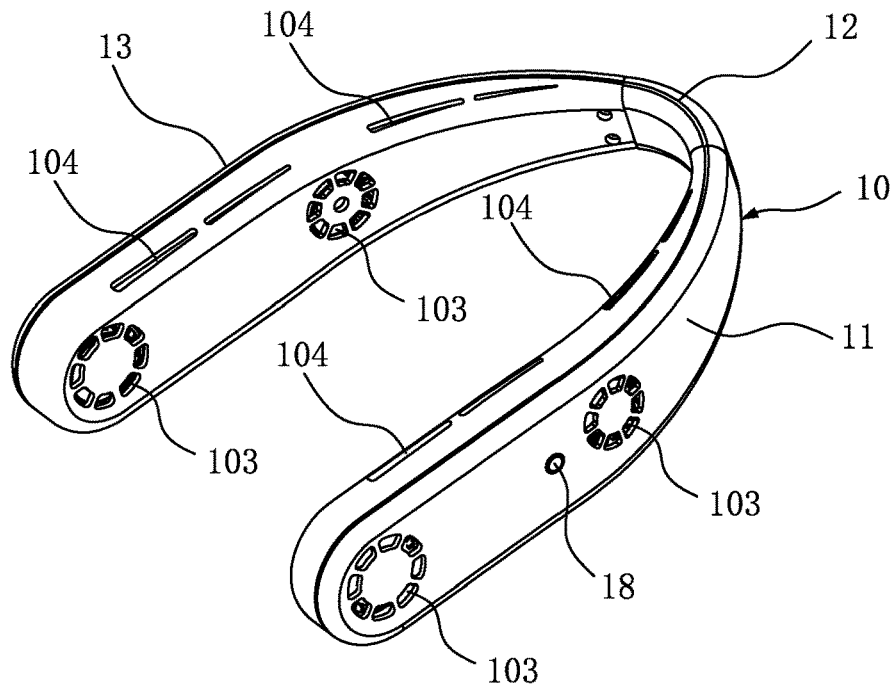
FIG. 30 is a structural diagram of a portable blowing device according to Embodiment 10 of the present disclosure.
Figure 31:
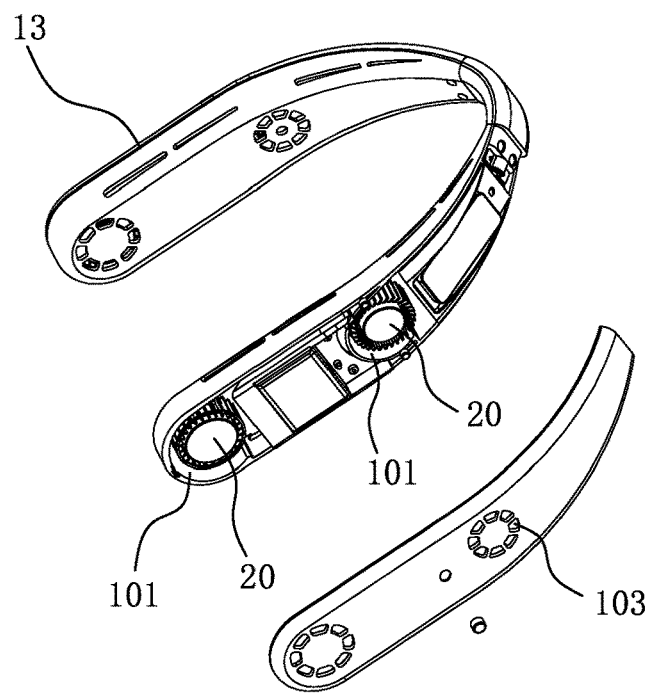
FIG. 31 is a partly exploded view of the portable blowing device according to Embodiment 10 of the present disclosure.
Figure 32:
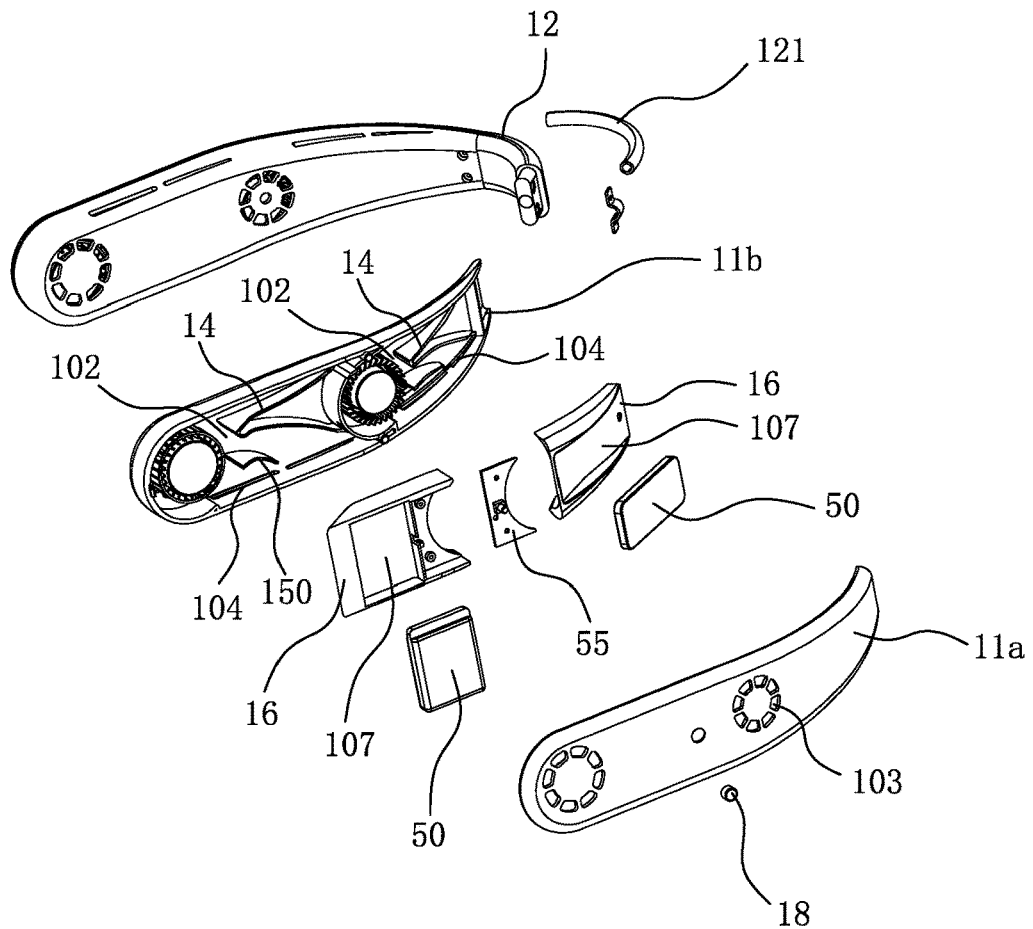
FIG. 32 is an exploded view of the portable blowing device according to Embodiment 10 of the present disclosure.

As shown in FIGS. 25-29, a portable blowing device provided in the present embodiment is a neck fan configured to be put on the neck of the human body. The neck fan comprises a flexible connector 12 and supports 13 respectively connected to opposite ends of the flexible connector 12. The structure of the support 13 of the neck fan provided in the present embodiment is the same as that of the support 13 of the above-mentioned neck fan in Embodiment 4, so the specific structure of the support 13 is not described here. The difference lies in the specific structure of the flexible connector 12, as shown in FIGS. 28 and 29. In the present embodiment, the flexible connector 12 comprises a bending and shaping member 122 and a flexible connection structure covering the bending and shaping member 122. The flexible connection structure comprises a soft rubber sleeve 121 and hard parts 125 arranged at opposite ends of the soft rubber sleeve 121 through injection molding. The hard part 125 comprises a fixing portion 45 located within an end of the soft rubber sleeve 121 through injection molding and a connecting portion 48 exposed from the soft rubber sleeve 121. The connecting portion 48 is used for connecting external components, such as for connecting the support 13. The flexible connection structure is also provided with a through hole 49 which sequentially penetrates through the hard part 125 at one end of the soft rubber sleeve 121, the soft rubber sleeve 121 and the hard part 125 at the other end of the soft rubber sleeve 121 in the axial direction of the flexible connection structure, and the through hole 49 allows the bending and shaping member 122 and elements such as leads connected between the circuit board and the fan 20 to pass through.

More specifically, the fixing portion 45 is tapered, the connecting portion 48 is square, and the fixing portion 45 and the connecting portion 48 are integrally formed. For example, the cross-sectional area of the fixing portion 45 gradually decreases from an end close to the connecting portion 48 to an end away from the connecting portion 48. The connecting portion 48 is connected to the larger end of the fixing portion 45, and a step 47 is formed between the connecting portion 48 and the larger end of the fixing portion 45. A surface of an end of the connecting portion 48 near the fixing portion 45 is provided with a positioning groove 482, and the soft rubber sleeve 121 can be integrally connected to the positioning groove 482 by injection molding, so that the positioning groove 482 is at least partially located in the soft rubber sleeve 121. In the process of injection molding, the melted material to form the soft rubber sleeve 121 flows to the hard part 125 and is connected with the hard part 125 after being cooled. For example, the soft rubber sleeve 121 encloses the fixing portion 45 of the hard part 125, so that the step 47 is enclosed by an end wall of the soft rubber sleeve 121, thus making the connection between the soft rubber sleeve 121 and the hard part 125 stable. Further, melted soft rubber flows into the positioning groove 482, and after the soft rubber solidifies and hardens, the connection between the soft rubber sleeve 121 and the hard part 125 is more stable. The hard part 125 cannot escape from the soft rubber sleeve 121 easily. The soft rubber sleeve 121 is made of a soft rubber material, so that the soft rubber sleeve 121 can bend and deform. The hard part 125 can be made of a hard rubber material or metal material, as long as the hard part 125 can hardly deform.

Two positioning holes 54 are formed in the connecting portion 48, neither of the positioning holes 54 communicates with the through hole 49. The positioning holes 54 are used for being fixedly connected with the support 13. During installation, opposite ends of the bending and shaping member 122 extend out of the through hole 49, the connecting portion 48 extends into a connecting end of the support 13, opposite end faces of the support 13 and the soft rubber sleeve 121 abut against each other, and an outer surface of the soft rubber sleeve 121 and an outer surface of the support 13 are connected in a smooth transition mode. With this arrangement, when the flexible connector is bent, a gap between the soft rubber sleeve 121 and the support 13 will not be enlarged so that the product looks more attractive, and the situation that the connecting portion 48 is separated from the soft rubber sleeve 121 and the support 13 falls off can be avoided. It should be understood that since the soft rubber sleeve 121 itself is made of a bendable and deformable soft rubber material, in other embodiments, the flexible connector 12 may not be provided with the bending and shaping member 122, so the through hole 49 may not be provided, and instead, the user may directly bend the soft rubber sleeve 121 to realize the bending deformation of the neck fan.

It should also be understood that in the above embodiments, the flexible connector is applied to a neck fan, and in other embodiments, the flexible connector of the present disclosure can also be applied to other products such as neck massagers and earphones.

To sum up, in the flexible connector provided by the present embodiment, the hard parts are arranged at opposite two ends of the soft rubber sleeve through injection molding, the fixing parts of the hard parts are embedded in the ends of the soft rubber sleeve, so that the ends of the soft rubber sleeve enclosing the fixing parts are hardly bent and deformed, which effectively prevents the situation that after the flexible connector is connected with external components through the connecting portion, when the flexible connector is bent, gaps are formed between the two ends of the soft rubber sleeve and the external components. The present embodiment also provides a neck fan with the flexible connector, and the neck fan further comprises supports connected to opposite two ends of the flexible connector. By arranging the hard parts at opposite two ends of the soft rubber sleeve through injection molding, when the flexible connector is bent, no gap appears between the soft rubber sleeve and an end face of the support, which makes the product look more attractive.

Embodiment 10

As shown in FIG. 30 to FIG. 34, a portable blowing device provided in Embodiment 10 of the present disclosure can be put on the neck of the human body, and comprises a body 10 and fans 20 arranged in the body 10. The fan 20 is preferably a centrifugal fan (turbofan).

In the present embodiment, the body 10 is C-shaped or U-shaped, and is adapted to the radian of the neck of the human body. The body 10 comprises a first support 11, a second support 13, and a flexible connector 12 connecting the first support 11 with the second support 13. A plurality of fans 20 are arranged in each of the first support 11 and the second support 13, for example, two fans 20 or three fans can be arranged in each of the first support 11 and the second support 13 to increase the airflow output of the portable blowing device. The flexible connector 12 is provided with a bending and shaping member 122 inside, and the bending and shaping member 122 is, for example, a shaping hose, so that the flexible connector 12 can maintain its bent shape after being bent.

Further, the first support 11 and the second support 13 of the body 10 are each provided with a receiving chamber 101, an air channel 102, an air inlet 103 and air outlets 104 corresponding to each fan 20, that is, each fan 20 has a receiving chamber 101, an air channel 102, an air inlet 103 and air outlets 104 corresponding thereto. The receiving chamber 101 is used for receiving the fan 20, and the receiving chamber 101 communicates with the air channel 102 and the air inlet 103. A side wall of the air channel 102 is provided with the air outlets 104, and the airflow generated by the fan 20 passes through the air channel 102 and then blows out from the air outlets 104. In the present embodiment, the air channels 102 of the first support 11 and the second support 13 are independent from each other and do not communicate with each other. The air inlets 103 are arranged on the inner and outer side walls of the first support 11 and the second support 13, and the air outlets 104 are arranged on the upper and lower side walls of the air channels 102. The air outlets 104 are elongated-shaped. Preferably, the width of the air outlets increases toward the fan 20, so as to increase the airflow speed at positions of the air outlets 103 away from the fan 20.

Further, the body 10 is provided with an air guiding member 14 in each air channel 102, and the air guiding member 14 is connected to the inner and outer side walls of the air channel 102 and thus divides the air channel 102 into a first air channel 102a and a second air channel 102b. The side walls of the first air channel 102a and the second air channel 102b are both provided with air outlets 104, and the airflow generated by the fan 20 is guided to the air outlets 104 in the upper and lower side walls of the air channel 102 through the air guiding member 14. The air guiding member 14 comprises a first guiding plate 141 and a second guiding plate 142, one ends of the first guiding plate 141 and the second guiding plate 142 close to the fan 20 are connected with each other, and the other ends of the first guiding plate 141 and the second guiding plate 142 away from the fan 20 are connected to the side walls of the air channel 102. The first guiding plate 141 is used to define the shape of the first air channel 102a, so that the first air channel 102a is gradually enlarged from an end away from the fan 20 toward the fan 20, and the second guiding plate 142 is used to define the shape of the second air channel 102b, so that the second air channel 102b is gradually enlarged from an end away from the fan 20 toward the fan 20. Thus, the airflow generated by the fan 20 is gradually compressed after entering the first air channel 102a and the second air channel 102b, forming an air squeeze effect, whereby a strengthened airflow is generated at the air outlets 103 away from the fan 20.

Figure 33:
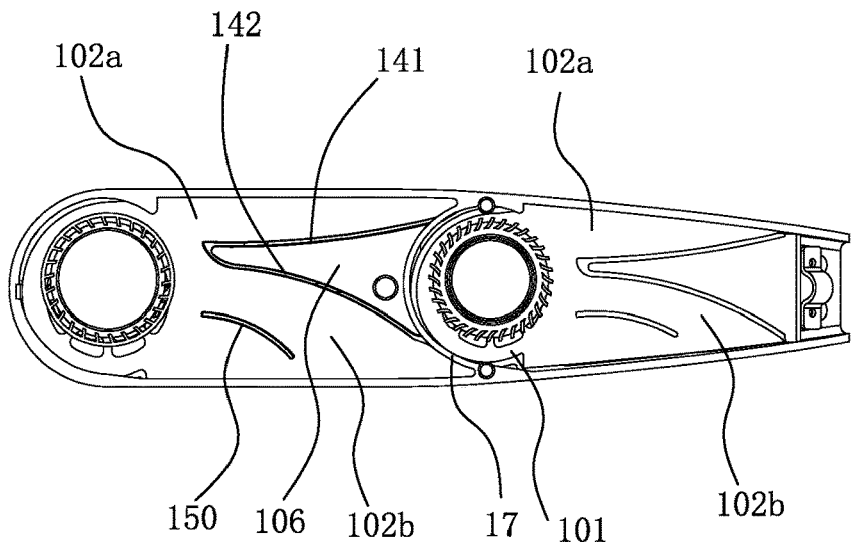
FIG. 33 is a side view of a first inner housing according to Embodiment 10 of the present disclosure.
Figure 34:
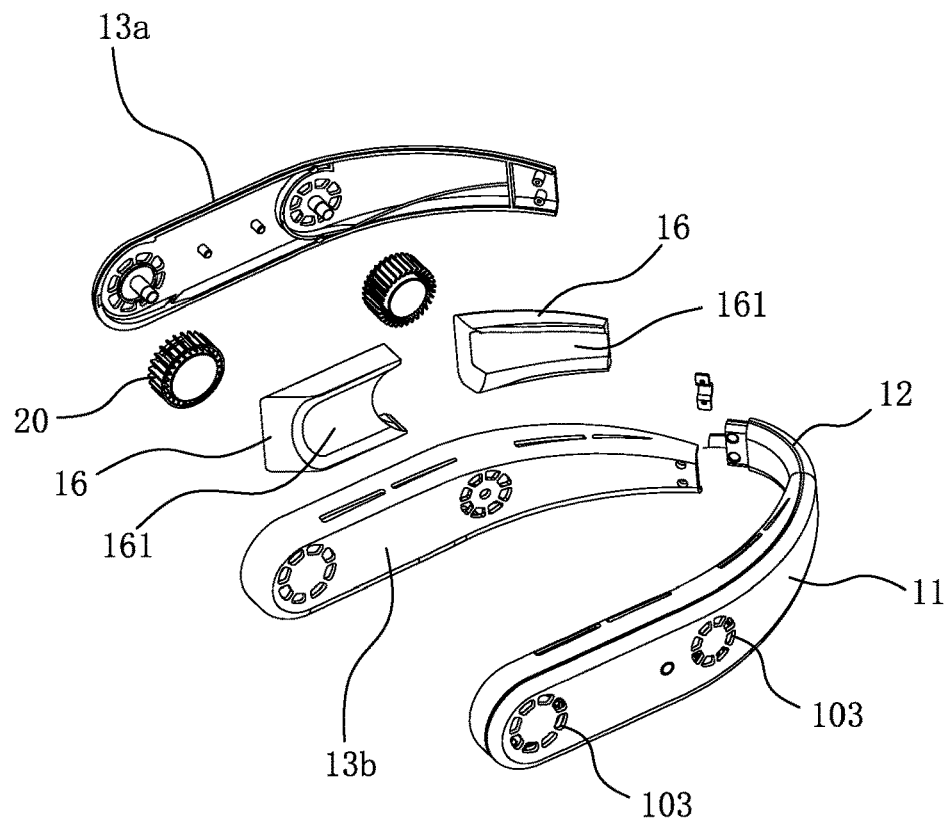
FIG. 34 is another exploded view of the portable blowing device according to Embodiment 10 of the present disclosure.

Further, referring to FIG. 33, the air guiding member 14 is of a V-shaped structure or Y-shaped structure, and both the first guiding plate 141 and the second guiding plate 142 are curved. The first guiding plate 141 bends toward the side away from the second guiding plate 142, and the second guiding plate 142 bends toward the side away from the first guiding plate 141. The volume of the first air channel 102a is smaller than that of the second air channel 102b, that is, the proportion of the first air channel 102a in the air channel 102 is smaller than the proportion of the second air channel 102b in the air channel 102. A curved guide vane 150 is arranged in the second air channel 102b. The guide vane 150 is bent away from the second guiding plate 142. An end of the guide vane 150 close to the fan 20 is higher than an end of the guide vane 150 away from the fan 20. That is, the distance between the end of the guide vane 150 close to the fan and the lower side wall of the support is greater than that between the end of the guide vane 150 away from the fan and the lower side wall of the support. The two sides of the guide vane 150 in the width direction closely contact with the inner walls of the second air channel 102b, and the guide vane 150 is configured to divide/guide the airflow in the second air channel 102b to prevent all the airflow from flowing out from the air outlets of the second air channel 102b close to the fan. In other embodiments, the guide vane 150 can also be implemented as a straight plate, and the end of the guide vane 150 close to the fan 20 is higher than the end of the guide vane 150 away from the fan 20, that is, the end of the guide vane 150 away from the fan 20 is closer to the bottom wall of the air channel 102 than the end close to the fan 20.

In the present embodiment, the portable blowing device further comprises a battery 50, and a wind shield 16 and a receiving cavity 107 are further arranged in the body 10, wherein the wind shield 16 separates the air channel 102 from the receiving cavity 107, and the battery 50 is arranged in the receiving cavity 107 and electrically connected with the fan 20. The air guiding member 14 is arranged perpendicular to the major surface of the wind shield 16. One side of the wind shield 16 facing the air channel 102 is provided with an airflow guiding slot 161, and preferably, the guiding slot 161 gradually becomes larger from an end away from the fan 20 toward the fan 20.

Further, the first support 11 comprises a first outer housing 11a and a first inner housing 11b, and the second support 13 comprises a second outer housing 13a and a second inner housing 13b. In the present embodiment, the receiving cavity 107 is located between the wind shield 16 and the outer housings (the first outer housing 11a and the second outer housing 13a), and the battery 50 is disposed in the receiving cavity 107.

In the present embodiment, both the first support 11 and the second support 13 of the body 10 are provided with arc-shaped separators 17 (FIG. 33). The separators 17 are arranged between two adjacent fans 20 in each housing (the first support 11 and the second support 13) and configured to separate the air channels 102 corresponding to the two adjacent fans 20. The separators 17 serve as side walls of the receiving chambers 101 corresponding to the fans 20 away from the end of the housing. In other embodiments, the separator 17 may be formed in a plate shape or other shapes. Specifically, as shown in FIG. 33, taking the first support 11 as an example, the two fans 20 are respectively arranged in the two receiving chambers 101, and the separator 17 is used to separate the receiving chamber 101 of one fan 20 from the air channel 102 of the other fan 20, that is, to separate the air channels 102 of the two fans 20. Preferably, the air guiding member 14 in one of the air channels 102 is connected with the separator 17 to form an integral structure, so that one ends of the first guiding plate 141 and the second guiding plate 142 of the air guiding member 14 away from the fan 20 are indirectly connected with the upper and lower side walls of the air channel 102 through the separator 17, and the separator 17 is arranged close to one of the fans 20 and bends toward the fan 20. Of course, in other embodiments, the ends of the first guiding plate 141 and the second guiding plate 142 of the air guiding member 14 away from the fan 20 can also be directly connected with the upper and lower side walls of the air channel 102. A cavity 106 is formed between the first air channel 102a and the second air channel 102b, and the cavity 106 is spaced apart from the first air channel 102a and the second air channel 102b. The cavity 106 can effectively absorb and restrain the noise caused by the airflow generated by the fan 20 hitting the air guiding member 14.

Further, the portable blowing device comprises a circuit board 55. A switch button 18 configured for controlling the fan 20 is arranged on the body 10. The circuit board 55 is electrically connected with the fan 20, the battery 50 and the switch button 18. In the present embodiment, the switch button 18 is arranged on the first support 11, and the circuit board 55 is arranged between the two wind shields 16. The switch button 18 is used to control the start and stop of the fan 20 and the airflow speed. In the present embodiment, the portable blowing device is also provided with an indicator light (not shown), a charging interface (not shown), etc., which will not be described in detail here.

Embodiment 11

Figure 35:
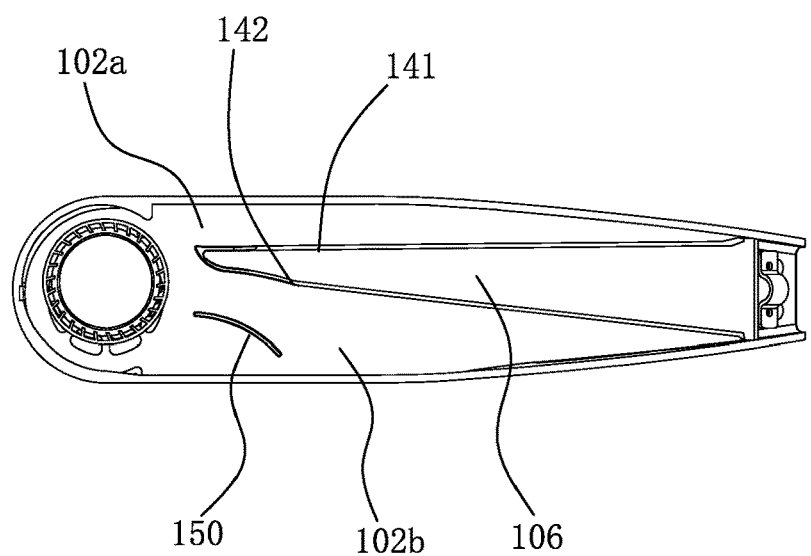
FIG. 35 is a side view of a first inner housing of a portable blowing device according to the Embodiment 11 of the present disclosure.

FIG. 35 is a side view of a first inner housing of a portable blowing device according to the Embodiment 11 of the present disclosure. As shown in FIG. 35, a portable blowing device provided in the present embodiment is basically the same as the portable blowing device in Embodiment 10 (shown in FIG. 30 to FIG. 34), except that in the present embodiment, the first support 11 and the second support 13 are each provided with only one fan 20, and one receiving chamber 101, one air channel 102, one air guiding member 14, one guide vane 150 and one wind shield 16 corresponding to the fan 20. The inner and outer side walls of the receiving chamber 101 are provided with air inlets 103, and the upper and lower side walls of the air channel 102 are provided with air outlets 104. In the present embodiment, the first support 11 and the second support 13 need not be provided with the separators 17.

Embodiment 12

Figure 36:
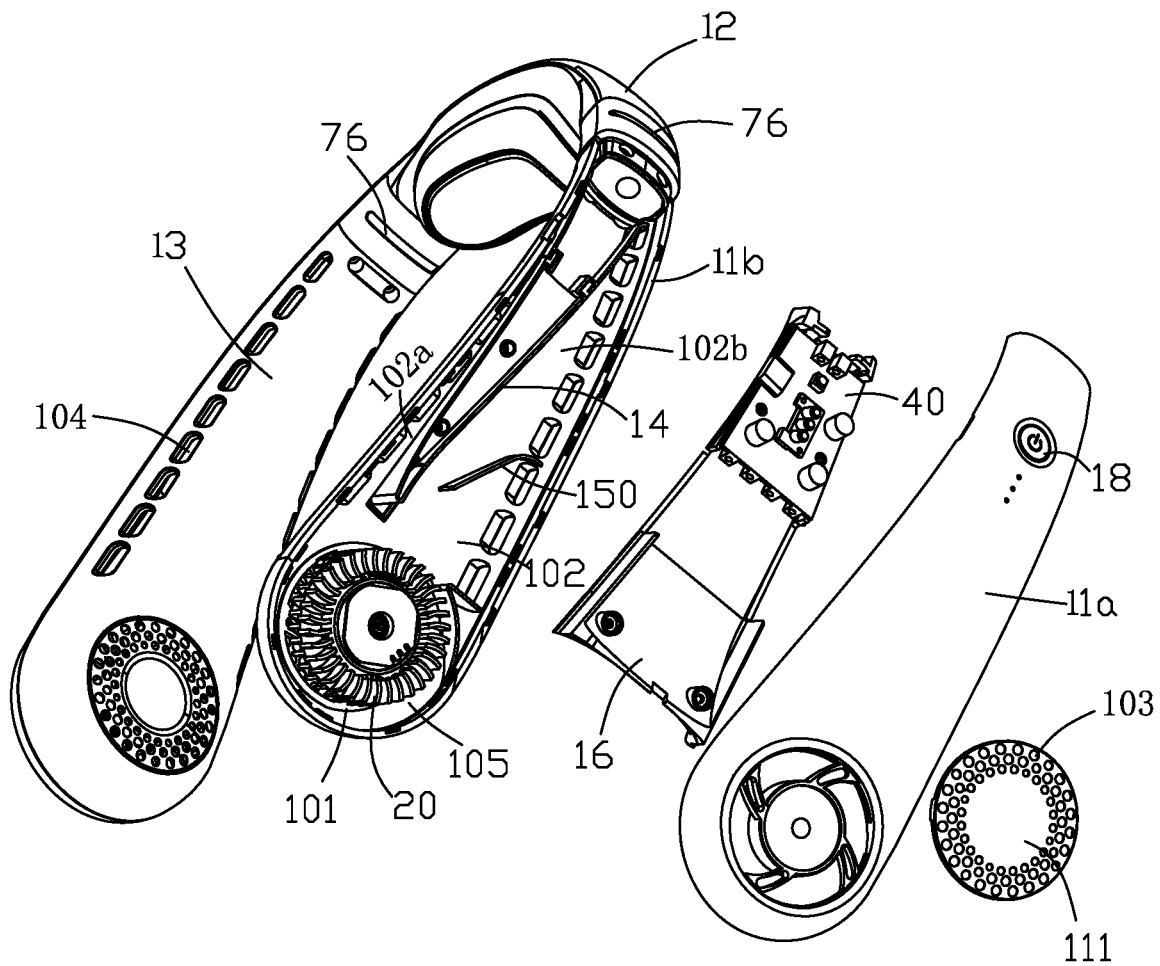
FIG. 36 is a structural diagram of a portable blowing device according to Embodiment 12 of the present disclosure.
Figure 37:
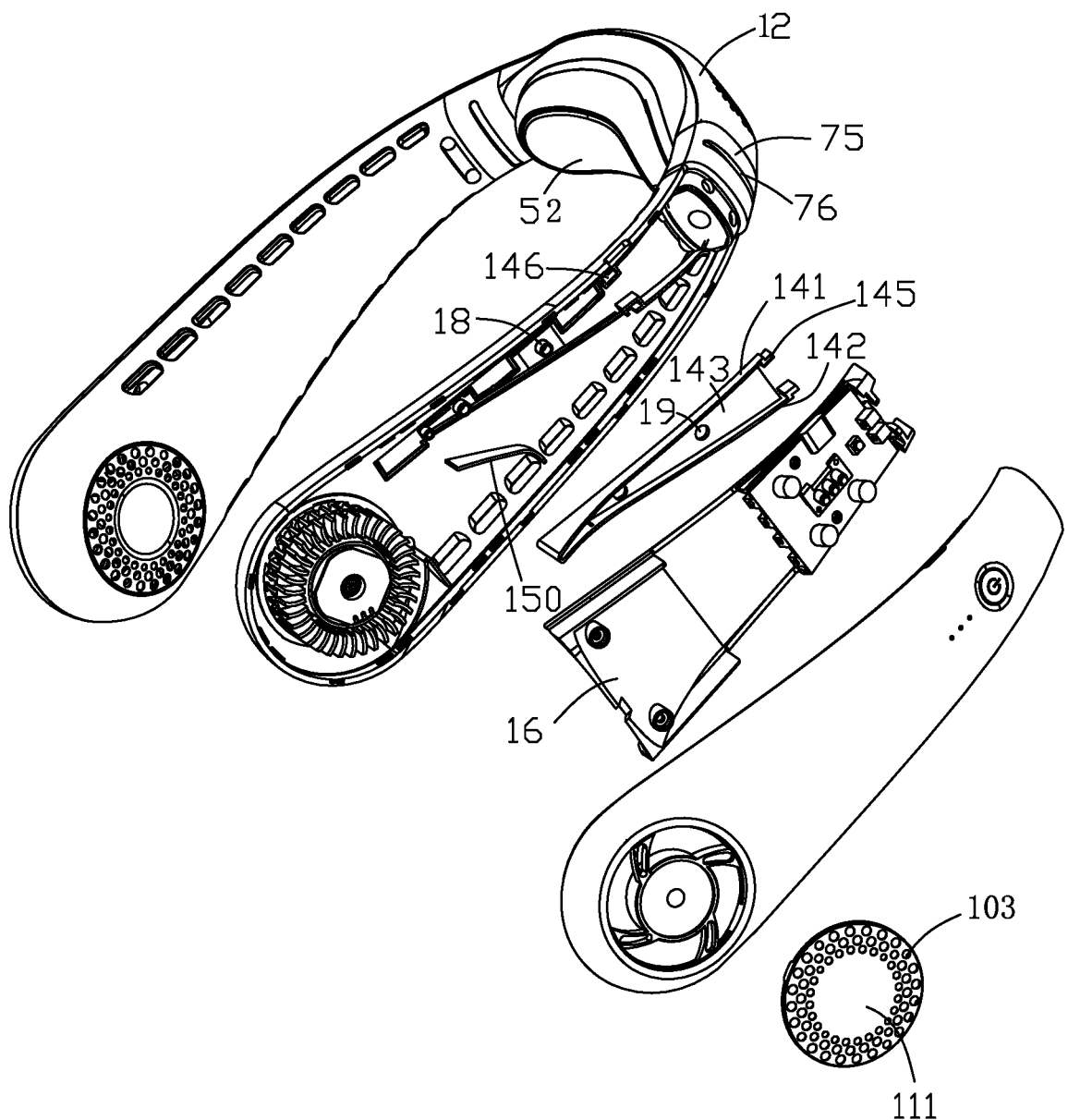
FIG. 37 is a partly exploded view of the portable blowing device of FIG. 36.
Figure 38:
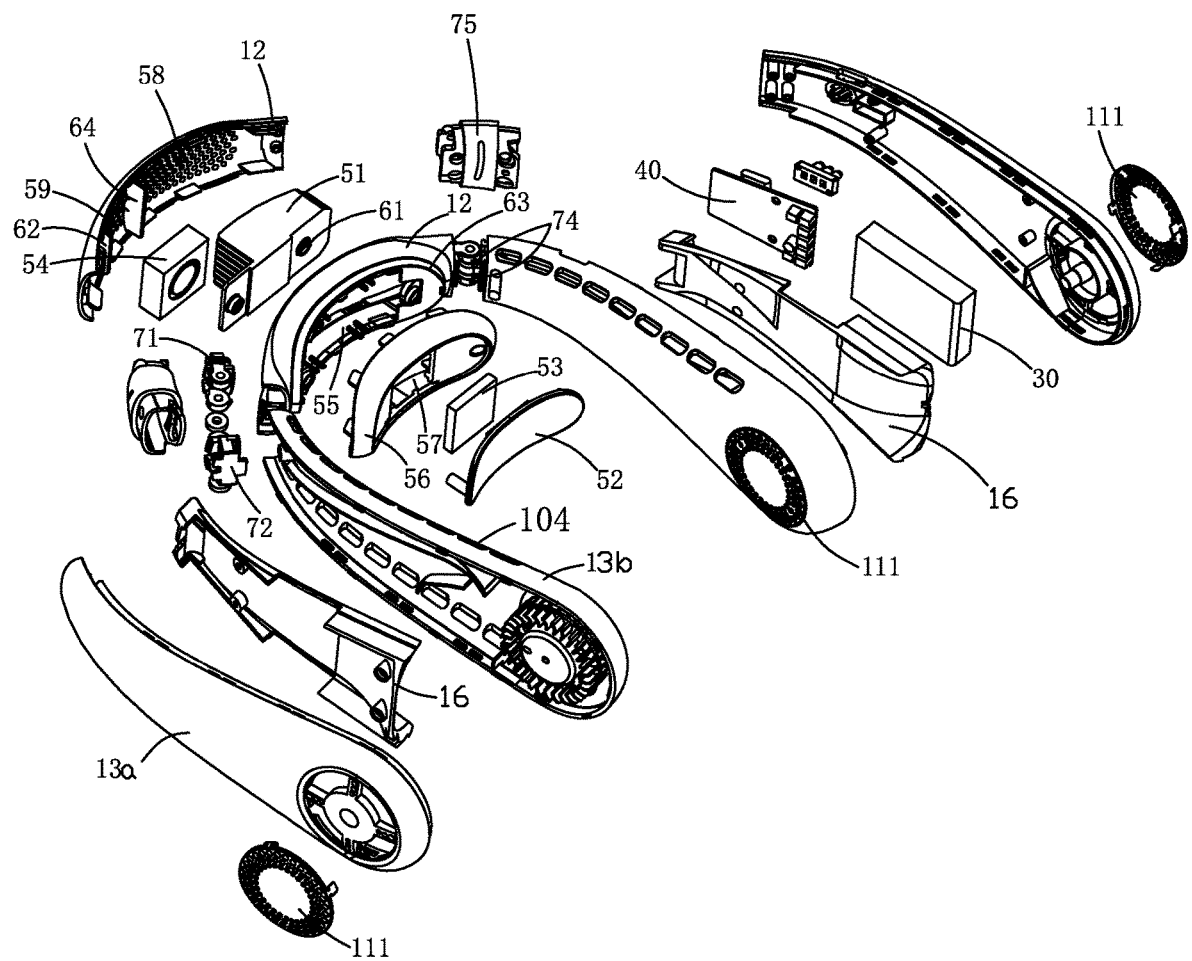
FIG. 38 is an exploded view of the portable blowing device of FIG. 36.

As shown in FIG. 36 to FIG. 38, a portable blowing device provided in the present embodiment is basically the same as the portable blowing device in Embodiment 10 (as shown in FIG. 30 to FIG. 34). In the present embodiment, the portable blowing device also comprises a first support 11, a second support 13 and a connector 12 connecting the first support 11 with the second support 13, except that the first support 11 and the second support 13 are each provided with only one fan 20, and one receiving chamber 101, one air channel 102, one air guiding member 14, one guide vane 150 and one wind shield 16 corresponding to the fan 20. The inner and outer side walls of the receiving chamber 101 are provided with air inlets 103, the air channel 102 is divided into a first air channel 102a and a second air channel 102b by the air guiding member 14, the side walls of the first air channel 102a and the second air channel 102b are both provided with air outlets 104. The first support 11 comprises a first outer housing 11a and a first inner housing 11b, and the second support 13 comprises a second outer housing 13a and a second inner housing 13b. In the present embodiment, the air guiding members 14 in the first support 11 and the second support 13 are respectively assembled and fixed to the first inner housing 11b and the second inner housing 13b (i.e., the side wall of the air channel 102), and the split design facilitates the molding and manufacturing of the first inner housing 11b, the second inner housing 13b and the air guiding members 14. Specifically, the air guiding member 14 further comprises a connecting plate 143 connecting the first guiding plate 141 with the second guiding plate 142, wherein the connecting plate 143 is generally triangular and fixed to the inner side wall of the first inner housing 11b/the second inner housing 13b (i.e., the side wall of the air channel 102), and the first guiding plate 141 and the second guiding plate 142 extend perpendicularly from opposite side edges of the connecting plate 143 and are sandwiched between the two side walls of the air channel 102. Preferably, the ends of the first guiding plate 141 and the second guiding plate 142 facing the fan 20 are connected to form a V-shape. In the direction away from the fan 20, the first guiding plate 141 extends obliquely toward the upper side wall of the first support 11 and the second guiding plate 142 extends obliquely toward the lower side wall of the first support 11, and the distance between the first guiding plate 141 and the second guiding plate 142 increases gradually in the direction away from the fan 20. In this way, the first air channel 102a and the second air channel 102b both have a tapered structure in the airflow direction (i.e., in the direction away from the fan 20), which facilitate to form a squeezing effect on the airflow, so that the airflow can have a higher airflow speed and greater air pressure at the air outlets 103.

Further, the inner side wall of the first inner housing 11b/second inner housing 13b is provided with a positioning stud 18, the connecting plate 143 is correspondingly provided with a positioning hole 19, and the positioning stud 18 is inserted in the positioning hole 19 to thereby position the connecting plate 143 on the inner side wall of the first inner housing 11b/second inner housing 13b. In the present embodiment, the first guiding plate 141 and the second guiding plate 142 of the air guiding member 14 each comprise two sections, one section is integrally formed with/connected to the inner side wall of the first inner housing 11b/the second inner housing 13b, that is, the section away from the fan 20 is integrally formed with/connected to the inner side wall of the first inner housing 11b/the second inner housing 13b, and the other section is connected to the connecting plate 143. Specifically, the tail ends of the sections of the first guiding plate 141 and the second guiding plate 142 near the fan 20 are provided with L-shaped locking parts 145, and the starting ends of the sections of the first guiding plate 141 and the second guiding plate 142 away from the fan 20 are provided with L-shaped locking grooves 146, and the L-shaped locking parts 145 are respectively locked in the L-shaped locking grooves 146 to thereby form the completed first guiding plate 141 and the completed second guiding plate 142, namely the air guiding member 14.

Referring to FIG. 36, in the present embodiment, the axial center of the fan 20 and the center of the receiving chamber 101 are eccentrically arranged with a gap 105 formed between the fan 20 and the side wall of the receiving chamber 101. The gap 105 is C-shaped and gradually widens in the rotating direction of the fan 20. The gap 105 has opposite two openings at both ends thereof. In the present embodiment, the rotating direction of the fan 20 as shown in FIG. 36 is clockwise, and a larger one of openings of the gap 105 faces the first air channel 102a. The airflow generated by the fan 20 blows obliquely toward the lower side wall of the air channel 102, that is, the airflow generated by the fan 20 tends to flow into the second air channel 102b, but the airflow generated by the fan 20 arrives at the first air channel 102a firstly and then arrives at the second air channel 102b. The volume of the first air channel 102a is designed to be smaller than that of the second air channel 102b, so that the air intake volume of the first air channel 102a is equal to that of the second air channel 102b.

In the present embodiment, the first support 11 and the second support 13 are respectively rotatably connected with opposite ends of the connector 12 through rotating structures, that is, the first support 11 and the second support 13 can rotate relative to the connector 12 to adjust the width between the first support 11 and the second support 13, so that the user can easily put on the portable blowing device or remove the portable blowing device from the neck of the human body. The connector 12 is also provided with a semiconductor temperature control device which comprises a heat sink 51 arranged in the connector 12, a heat conducting member 52 arranged on the inner side wall of the connector 12, a semiconductor refrigeration sheet 53 mounted between the heat sink 51 and the heat conducting member 52, and a cooling fan 54 arranged at one end of the heat sink 51. More specifically, the inner side wall of the connector 12 defines an opening 55 corresponding to the heat sink 51. A mounting enclosure 56 is mounted to the opening 55. The mounting housing 56 can be fixed to the inner side wall of the connector 12 through interlocking means or the like. The mounting enclosure 56 is provided with a mounting recess 57 for receiving the semiconductor refrigeration sheet 53. The heat conducting member 52 is in an arc shape adapted to the neck of the human body, and the heat conducting member 52 is connected to one side of the mounting enclosure 56 away from the heat sink 51, for example, through interlocking means or the like. The heat sink 51 comprises a connecting plate and a plurality of cooling fins extending from the connecting plate in a direction away from the semiconductor refrigeration sheet 53, wherein the plurality of cooling fins are arranged at intervals, and a radiating groove is formed between two adjacent cooling fins. In the length direction, one end of the connecting plate extends beyond the cooling fins, the cooling fan 54 is at least partially located on the other end of the connecting plate, and an air outlet of the cooling fan 54 faces the radiating groove to cool the cooling fins. After installation, a cold end face of the semiconductor refrigeration sheet 53 is attached to the heat conducting member 52, and a hot end face of the semiconductor refrigeration sheet 53 is attached to the connecting plate of the heat sink 51. Heat dissipation holes 58 and air inlets 59 respectively corresponding to the heat sink 51 and the cooling fan 54 are formed on the outer side wall of the connector 12. Heat accumulated at the heat sink 51 is dissipated from the heat dissipation holes 58, and air enters the cooling fan 54 through the air inlets 59.

In order to further stabilize the accurate positioning of the semiconductor temperature control device and its components, a mounting hole 61 is formed in the connecting plate, a through hole is formed in the inner side wall of the connector 12 and a screw hole is formed in the mounting housing 5. A screw is passed through the mounting hole 61 and the through hole of the connector 12 to be fixed in the screw hole of the mounting housing 56, so that the heat sink 51 and the mounting housing 56 are fixed to the connector 12. The inner side wall of the connector 12 is also provided with a positioning piece 62, and the positioning piece 62 abuts against a side edge of the cooling fan 54 to install and position the cooling fan 54, so that the cooling fan 54 can be stably installed.

Preferably, a decorative ring 63 is arranged on a peripheral wall of the opening 55. When the mounting enclosure 56 is connected to the connector 12, the decorative ring 63 has a decorative function to make the product look more attractive.

Further, partition plates 64 are arranged between the heat dissipation holes 58 and the air inlets 59, and the partition plates 64 are located between the heat sink 51 and the cooling fan 54. The partition plate 64 has a blocking function and can prevent the heat from the heat sink 51 from returning to the air inlets of the cooling fan 54 and affect heat dissipation. In addition, the partition plates 64 also coordinate with the positioning piece 62 to position the cooling fan 54, so that the cooling fan 54 is clamped between the positioning piece 62 and the partition plates 64 stably.

Specifically, the rotating structure comprises a first connecting member 71 and a second connecting member 72, one ends of the first connecting member 71 and the second connecting member 72 cooperate with each other through a pivoting structure consisted of a rotating shaft and a shaft hole to realize rotary connection, and the other ends are respectively fixedly connected with the connector 12 and the first support 11/second support 13, for example, through screws or snap connection means, so that the first support 11 and the second support 13 can rotate inwardly or outwardly relative to the connector 12. Specifically, the first connecting member 71 comprises a first stationary part and two first pivot parts connected to one end of the first stationary part and arranged at intervals, wherein the first pivot part is provided with a shaft hole; and the second connecting member 72 comprises a second stationary part and a second pivot part connected to one end of the second stationary part, and the second pivot part is provided with a shaft hole. During installation, the first stationary part extends into the end of the connector 12 for being fixed with the connector 12, the second stationary part extends into the ends of the first support 11/the second support 13 for fixing therewith, the second pivoting part extends between the two first pivoting parts, and a rotating shaft is inserted into the shaft hole, thereby realizing rotary connection between the first connecting member 71 and the second connecting member 72.

Preferably, the rotating structure further comprises a damping member for increasing the frictional resistance of the first support 11/second housing 12 when the first support 11/second support 12 rotating relative to the connector 12, and enabling the first support 11/second support 13 to stay at any rotating position stably relative to the connector 12, thereby preventing the first support 11/second support 13 from rotating relative to the connector 12 arbitrarily (without external force). In the illustrated embodiment, the damping member is a damping ring 74. There are two damping rings 74 which are respectively sandwiched between the second pivot part and the two first pivot parts.

Since the joint of the first connecting member 71 and the second connecting member 72 is exposed from the connector 12 and the first housing 11/second support 13, in order to ensure the aesthetic appearance of the product, in the illustrated embodiment, the rotating structure is enclosed with a silicone sleeve 75, and opposite ends of the silicone sleeve 75 are connected with the ends of the first support 11 and the second support 12 respectively. As the silicone sleeve 75 is made of a soft material, it will be elastically deformed along with the rotation of the rotating structure, so it will not affect the rotation of the rotating structure. The outer surfaces of opposite ends of the silicone sleeve 75 can be configured to be in smooth transition with the outer surfaces of the first body 14 and the second body 16, so as to enhance the aesthetic appearance of the product. Preferably, some grooves 76 facilitating deformation of the silicone sleeve 75 may be formed on the silicone sleeve 75, so that the silicone sleeve 75 is more easily bent and deformed along with the deformation of the rotating structure when the rotating structure rotates.

In the present embodiment, metal sheets 111 are respectively installed on the side walls of the receiving chamber 101 corresponding to both sides of the fan 20, and the air inlets 103 are air inlet meshes provided on the metal sheets 111, thus effectively preventing the user's hair from entering the fan 20.

The above-mentioned embodiments merely represent several implementations of the present application, and the descriptions thereof are more specific and detailed, but they shall not be understood as a limitation on the scope of the present application. It should be noted that, for those of ordinary skill in the art, variations and improvements may still be made without departing from the concept of the present application, and all of which shall fall into the protection scope of the present application. Therefore, the scope of protection of the present application shall be subject to the appended claims.

What is claimed is:

1. A portable blowing device for being hung around a neck of a user, comprising:
- a body comprising supports; and
- a fan arranged in the body;
- wherein an air channel communicating with the fan is arranged in the supports, and an air guiding member is arranged in the air channel to divide the air channel into a first air channel and a second air channel, a side wall of the support surrounding the air channel comprises a first section and a second section located on opposite sides of the air guiding member, the first section is provided with first air outlets communicating with the first air channel, and the second section is provided with second air outlets communicating with the second air channel.

2. The portable blowing device according to claim 1, wherein the support comprises an inner side wall close to the neck of the user and an outer side wall away from the neck of the user, the first air outlets and the second air outlets are arranged on the inner side wall, a starting end of the air guiding member divides an inlet of the air channel into a first air inlet and a second air inlet, the first air inlet and the second air inlet respectively communicate with the first air channel and the second air channel, and an area of the first air inlet is smaller than that of the second air inlet.

3. The portable blowing device according to claim 2, wherein a guide vane is arranged in the second air channel.

4. The portable blowing device according to claim 3, wherein a distance between an end of the guide vane close to the fan and a lower side wall of the support is greater than a distance between an end of the guide vane away from the fan and the lower side wall of the support; or
- two sides of the guide vane in a width direction thereof closely contact with an inner wall of the second air channel.

5. The portable blowing device according to claim 1, wherein the first air channel is gradually enlarged from an end away from the fan toward the fan, and the second air channel is gradually enlarged from an end away from the fan toward the fan.

6. The portable blowing device according to claim 5, wherein the air guiding member comprises a first guiding plate and a second guiding plate, ends of the first guiding plate and the second guiding plate close to the fan are connected with each other, and ends of the first guiding plate and the second guiding plate away from the fan are respectively connected with a side wall of the air channel.

7. The portable blowing device according to claim 6, wherein the air guiding member further comprises a connecting plate connecting the first guiding plate with the second guiding plate, one of the connecting plate and the side wall of the support surrounding the air channel is formed with a positioning stud, and the other one is formed with a positioning hole for insertion of the positioning stud.

8. The portable blowing device according to claim 5, wherein the body further comprises a connector, the supports are respectively connected to opposite ends of the connector, a semiconductor temperature control device is arranged in the connector, and the semiconductor temperature control device comprises a heat sink arranged in the connector, a heat conducting member arranged on an inner side wall of the connector, a semiconductor refrigeration sheet attached between the heat sink and the heat conducting member, and a cooling fan arranged at one end of the heat sink.

9. The portable blowing device according to claim 1, wherein the body comprises a flexible connector and supports respectively connected to opposite ends of the flexible connector, the fan and the air channel are disposed in the supports, and the flexible connector comprises a bending and shaping member inside.

* * * * *